United States Patent
Smith et al.

(10) Patent No.: US 9,895,399 B2
(45) Date of Patent: Feb. 20, 2018

(54) REPAIR OF PERIPHERAL NERVE INJURY

(71) Applicant: The Trustees of The University of Pennsylvania, Philadelphia, PA (US)

(72) Inventors: Douglas H. Smith, Boothwyn, PA (US); Kacy D. Cullen, Media, PA (US); John A. Wolf, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/764,450

(22) PCT Filed: Jan. 31, 2014

(86) PCT No.: PCT/US2014/014133
§ 371 (c)(1),
(2) Date: Jul. 29, 2015

(87) PCT Pub. No.: WO2014/121063
PCT Pub. Date: Aug. 7, 2014

(65) Prior Publication Data
US 2015/0352153 A1    Dec. 10, 2015

Related U.S. Application Data

(60) Provisional application No. 61/759,151, filed on Jan. 31, 2013, provisional application No. 61/785,309, filed on Mar. 14, 2013.

(51) Int. Cl.
*A61K 35/30* (2015.01)

(52) U.S. Cl.
CPC .................................. *A61K 35/30* (2013.01)

(58) Field of Classification Search
CPC .............................. A61K 35/30; C12N 5/0619
See application file for complete search history.

(56) References Cited

U.S. PATENT DOCUMENTS

2008/0226609 A1* 9/2008 Proschel ............... A61K 35/30
                                                    424/93.7
2011/0263504 A1* 10/2011 Cerami ................ C07K 14/505
                                                    514/15.4

OTHER PUBLICATIONS

Pfister et al. Development of transplantable nervous tissue constructs comprised of stretch-grown axons. J Neurosci Methods. May 15, 2006;153(1):95-103. Epub Dec. 5, 2005.*
Barbour, et al., "Supercharged End-to-Side Anterior Interosseous to Ulnar Motor Nerve Transfer for Intrinsic Musculature Reinnervation", J Hand Surg. 37(10), 2012, 2150-2159.
Farber, et al., "Supercharge Nerve Transfer to Enhance Motor Recovery", J Hand Surg. 38(3), 2013, 466-477.
Gordon, et al., "Accelerating Axon Growth to Overcome Limitations in Functional Recovery alter Peripheral Nerve Injury", Neurosurgery 65(4), 2009, A132-A144.
Gordon, et al., "Brief electrical stimulation accelerates axon regeneration in the peripheral nervous system and promotes sensory axon regeneration in the central nervous system", Motor Control 13(4), 2009, 412-441.
Gordon, et al., "The Basis for Diminished Functional Recovery after Delayed Peripheral Nerve Repair.", J Neurosci. 31(14), 2011, 5325-5334.
Gordon, "The physiology of neural injury and regeneration: The role of neurotrophic factors", J Commun Disord. 43 (4), 2010, 265-273.
Ladak, et al., "Side-to-side nerve grafts sustain chronically denervated peripheral nerve pathways during axon regeneration and result in improved functional reinnervation", Neurosurgery 68(6), 2011, 1654-1666.
Midha, et al., "Regeneration into Protected and Chronically Denervated Peripheral Nerve Stumps", Neurosurgery 57 (6), 2005, 1289-1299.
Scholz, et al., "Peripheral nerve injuries: An international survey of current treatments and future perspectives", J Reconstructive Microsurgery 25(6), 2009, 339-344.
Smith, "Stretch Growth of Integrated Axon Tracts: Extremes & Exploitations", Progress in Neurobiology 89(3), 2009, 231-239.
Sulaiman, et al., "Role of Chronic Schwann Cell Denervation in Poor Functional Recovery after Nerve Injuries and Experimental Strategies to Combat It", Neurosurgery 65(4), 2009, A105-A114.

* cited by examiner

*Primary Examiner* — Gregory S Emch
(74) *Attorney, Agent, or Firm* — Saul Ewing Arnstein & Lehr LLP; Kathryn Doyle

(57) ABSTRACT

The invention relates to methods and compositions for maintaining the pro-regenerative capacity of distal nerve segments following nerve injury.

25 Claims, 26 Drawing Sheets

Surgically implant into nerve lesion

16 Weeks later (tube degraded; nerve regenerated)

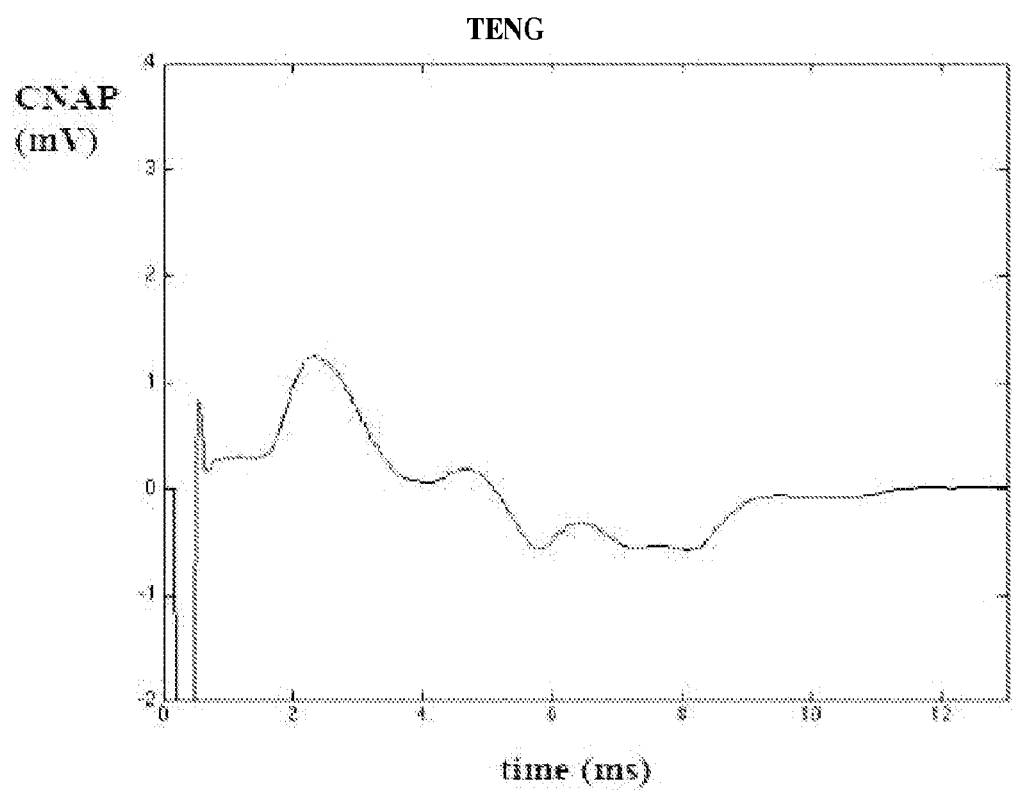

bar = 100 µm          bar = 100 µm          bar = 50 µm bars = 100 μm

REPAIR OF PERIPHERAL NERVE INJURY

CROSS-REFERENCE TO RELATED APPLICATION

This application is a U.S. national phase application under 35 U.S.C. § 371 claiming benefit to International Patent Application No. PCT/US2014/014133, filed on Jan. 31, 2014, which is entitled to priority under 35 U.S.C. § 119(e) to U.S. Provisional Patent Application No. 61/759,151, filed Jan. 31, 2013, and U.S. Provisional Patent Application No. 61/785,309, filed Mar. 14, 2013, each of which application is hereby incorporated herein by reference in its entirety.

STATEMENT REGARDING FEDERALLY SPONSORED RESEARCH OR DEVELOPMENT

This invention was made with government support under grant numbers NS048949, NS038104, NS056202, and NRSA NS043126 awarded by the National Institutes of Health; grant number SC090019 through the Department of Defense (DoD); and an award by the Armed Forces Institute of Regenerative Medicine through the DoD. The government has certain rights in the invention.

FIELD OF THE INVENTION

The invention relates to methods and compositions for maintaining the pro-regenerative capacity of distal nerve segments following nerve injury.

BACKGROUND OF THE INVENTION

Injuries to peripheral nerves can be caused by trauma, surgery, cancer and by congenital anomalies. Injuries to peripheral nerves can be also caused by radiation therapy, chemotherapy, metabolic/endocrine complications, inflammatory and autoimmune diseases, vitamin deficiencies, infectious diseases, toxic causes, accidental exposure to organic metals and heavy metals, drugs, amputations and disease or condition relating to a loss of motor or sensory nerve function. Nerve injury or lesion may include nerve transection, crush, compression, stretch, laceration (sharps or bone fragments), ischemia and blast. In addition, nerve injury or lesion may result from damage or disruption of the neuronal axons. Injuries to peripheral nerves can be also caused by radiation therapy, chemotherapy, metabolic/endocrine complications, inflammatory and autoimmune diseases, vitamin deficiencies, infectious diseases, toxic causes, accidental exposure to organic metals and heavy metals, drugs, amputations and disease or condition relating to a loss of motor or sensory nerve function. Nerve injury or lesion may include nerve transection, crush, compression, stretch, laceration (sharps or bone fragments), ischemia and blast. In addition, nerve injury or lesion may result from damage or disruption of the neuronal axons.

Peripheral nerve injury is a major source of morbidity and an area with significant medical need. Indeed, only 50% of patients achieve good to normal restoration of function following surgical repair, regardless of the strategy. Moreover, failure of nerve regeneration may necessitate amputation of an otherwise salvaged limb. This stems from the inadequacy of current PNI repair strategies, where even the "gold-standard" treatment—the nerve autograft—is largely ineffective for major nerve trauma, defined as loss of a large segment of nerve (i.e., >5 cm) or injury occurring closer to the spinal cord (e.g., shoulder, thigh) resulting in extremely long distances for axon regeneration to distal targets (e.g., hand, foot). Despite significant efforts, PNI repair has not progressed past nerve guidance tubes (NGTs) for the bridging of small gaps or come close to matching the performance of autografts. As a result, the field is in desperate need of a transformative technology for repair of peripheral nerve injury.

The key failing of all current strategies to functionally repair major nerve trauma is the inability to coax a sufficient number of axons to grow a substantial distance to reinnervate distal targets (e.g., hand) and restore function. To overcome this failing, repair strategies must address two major challenges: (1) encourage rapid regeneration of proximal axons and (2) maintain the pro-regenerative capacity of the distal nerve segment for regenerating axons.

Degeneration of the axon segments distal to a nerve injury site is an inevitable consequence of transection of or injury to the nerve; however, the supporting Schwann cells in the distal nerve segment survive and switch to a pro-regenerative phenotype to support axon growth. This pro-regenerative phenotype includes a change in cellular alignment to form parallel columns, providing tracts that serve as guides for regenerating axons. Unfortunately, the natural pro-regenerative environment degrades after several months without the presence of axons, thus depriving regenerating axons of their "road map" to an end target. This occurs when the time it takes to regenerate axons to infiltrate the distal segment is greater than the time the Schwann cells can maintain their pro-regenerative phenotype. Often, following long or proximal PNI, the pro-regenerative environment fails and there is incomplete functional recovery. For example, a patient with a PNI of the upper arm may regain elbow, but not hand function, due to the distance between the nerve injury and the end targets in the hand, which are often not reached by proximal axons before the distal environment is no longer pro-regenerative. In another example, a PNI is not treatable due to the large size of the nerve lesion or injury, irrespective of the lesion or injury location.

Various techniques for prolonging the pro-regenerative capacity of the distal nerve segment following nerve injury have been explored. These include providing neurotrophic factors (e.g., GDNF, BDNF, and TGF-beta) to the distal nerve segment; administering electrical stimulation to the nerve sheath in an attempt to stimulate acceleration of axon regeneration; and transferring a foreign sensory nerve or an adjacent healthy nerve to the denervated nerve sheath (known as "babysitting" techniques). However, such techniques are often limited by a lack of efficacy, particularly with regard to long-term efficacy. In addition, some of these techniques have the clear disadvantage of transecting a healthy nearby nerve for the purpose of transferring it to the adjacent denervated nerve stump.

Thus, there is a need in the art for more effective means of maintaining the pro-regenerative capacity of denervated distal nerve segments so that the effectiveness of current or future means of PNI repair can be increased. There is a particular need in the art for maintaining pro-regenerative capacity and alignment of Schwann cells in the denervated distal nerve segment long-term.

BRIEF SUMMARY OF THE INVENTION

In one aspect, the present invention provides compositions and methods for maintaining a distal nerve segment subsequent to a nerve injury, the method comprising contacting the distal nerve segment with a stretch-grown tissue-engineered nerve graft (TENG). In another aspect, the present invention provides compositions and methods for maintaining a distal nerve segment subsequent to a nerve injury, the method comprising delivering one or more neurons into the distal nerve segment. In one embodiment, the neurons are injected directly into one or more nerve fascicles in the distal nerve segment. In one aspect of the present invention, the methods provided maintain the pro-regenerative capacity of the distal nerve segment.

In one embodiment, the methods provided maintain a distal nerve segment subsequent to a nerve injury, wherein the nerve injury is present in a subject. In one embodiment, the subject is a human. In another embodiment, the subject is a non-human mammal, for example, a non-human primate (e.g., monkey, baboon, and chimpanzee), mouse, rat, rabbit, horse, dog cat, or pig. In another embodiment, the nerve injury comprises an injury to a peripheral nerve of a subject. In one embodiment, the injury to the peripheral nerve is caused by a peripheral neuropathy. In one embodiment, the injury to the peripheral nerve is caused by trauma. In one embodiment, the injury to the peripheral nerve is caused by cancer. In one embodiment, the injury to the peripheral nerve is caused by a surgery. In one embodiment, the injury to the peripheral nerve is a congenital anomaly. In another embodiment, the nerve injury comprises an injury to the spinal cord of a subject. In another embodiment, the nerve injury is caused by a disease or condition that may include, for example, amyotrophic lateral sclerosis, carpal tunnel syndrome, or any other disease or condition relating to a loss of motor or sensory nerve function. In one embodiment, the nerve injury is caused by an amputation. In one embodiment, the nerve injury is caused by complete or partial removal of an organ, tumor, r tissue. In one embodiment, the nerve injury comprises the complete transection of the nerve. In one embodiment, the nerve injury comprises the compression or crushing of a nerve segment. For example, in one embodiment, the nerve injury comprises an acute crush injury or a repetitive crush injury, or an acute compression injury or a repetitive compression injury. In one embodiment, the crush or compression injury creates or contributes to a distal environment that is non-permissive or resistant to axonal regeneration. In one embodiment, the nerve injury occurs during or as a result of a medical procedure, including a surgical procedure. For example, nerve injury may occur due to crushing, compression, bruising, inflammation, or transection of a nerve during surgery. For example, nerve injury may occur as a result of contacting the nerve with the scalpel; bruising, inflammation, stretching, crushing, or compression of the nerve due to contact with surgical equipment and/or patient positioning during surgery (for example, prolonged Trendelenburg positioning or brachial injury in laparascopic injury due to positioning of patient arms). In one embodiment, nerve injury can occur as a result of radiation therapy (e.g., brachial plexopathy) or chemotherapy. In one embodiment, nerve injury can occur as a result of metabolic/endocrine complications including diabetes; inflammatory and autoimmune diseases; vitamin deficiencies including vitamins B6 and B12; infectious diseases including Lyme disease, herpes viruses, HIN and hepatitis C; and toxic causes, such as alcoholism. In one embodiment, nerve injury can occur as a result of accidental exposure to organic metals and heavy metals (for example, lead, arsenic and mercury). In one embodiment, nerve injury can occur as a result of drugs (for example, heart and blood pressure medications such as, for example, amiodarone, hydralazine and perphexiline; drugs used to treat infections such as, for example, chloroquine, isoniazid, metronidazole, nitrofurantoin, thalidomide; drugs used to treat autoimmune disease such as, for example, etanercept, infliximab and leflunomide; drugs used to treat skin conditions such as, for example, dapasone; anticonvulsants such as, for example, phehytoin; anti-alcohol drugs such as, for example disfulfiram; drugs to fight HIV such as, for example, didanosine, stavudine and zalcitabine; and colchicine).

In one embodiment, the nerve injury comprises the loss of a segment of a nerve. In another embodiment, the nerve injury comprises a nerve lesion of about 0.1, about 0.5, about 1.0, about 1.5, about 2.0, about 2.5, about 3.0, about 3.5, about 4.0, about 4.5, about 5.0, about 6.0, about 7.0, about 8.0, about 9.0, about 10.0, or more centimeters (cm) in length. In another embodiment, the nerve injury comprises a nerve lesion of less than 1 cm in length. In another embodiment, the nerve injury comprises a nerve lesion of at least about 1 cm in length. In another embodiment, the nerve injury comprises a nerve lesion of at least about 3 cm in length. In another embodiment, the nerve injury comprises a nerve lesion of at least about 5 cm in length.

In one embodiment, the nerve injury is less than about 1 cm from the distal target. In another embodiment, the nerve injury is at least about 1 cm, about 3 cm, about 10 cm, about 1 meter, or more than 1 meter from the distal target. Thus, in one embodiment, the distance between the distal position and the injury site is less than about 1 cm. In another embodiment, the distance between the distal position and the injury site is at least about 1 cm, at least about 3 cm, at least about 10 cm, at least about 1 meter, or more. In another embodiment, the methods provided herein are used to promote or maintain the pro-regenerative capacity of one or more distal nerve segments at one or more distal sites. Thus, in one embodiment, the methods provided promote or maintain the pro-regenerative capacity of at least 1, at least 2, at least 3, at least 5, at least 10, or more distal nerve segments or distal sites. In one embodiment, the method comprises contacting multiple distal nerve segments with one or more stretch-grown TENG, for example, contacting 2, 3, 4, 5, 10, 20, or more distal nerve segments with one or more stretch-grown TENG. In one embodiment, the method comprises injecting one or more neurons into multiple distal nerve segments, for example into 2, 3, 4, 5, 10, 20, or more distal nerve segments.

In one embodiment, the methods provided maintain the pro-regenerative capacity of the distal nerve segment for prolonged periods of time, for example, at least 6 about weeks, at least about 8 weeks, at least about 12 weeks, at least about 20 weeks, at least v30 weeks, at least about 1 year, at least about 1.5 years, at least about 2 years, at least about 2.5 years, or at least about 3 years. In another embodiment, the pro-regenerative capacity of the distal nerve segment is maintained until at least such time as proximal nerve axons reinnervate distal targets. In some embodiments, the distal target is a limb. In other embodiments, the distal target is a hand or a foot. In other embodiments, the distal target is an eyelid or tongue. In other embodiments, the distal target is a digit (e.g., a finger or a toe). In other embodiments, the distal target is an internal organ (e.g., lung, larynx or salivary gland). In other embodiments, the distal target is a tissue (e.g., muscle).

In one embodiment, provided herein are compositions and methods for maintaining a distal nerve segment subsequent to a nerve injury comprising contacting the distal nerve segment with one or more stretch-grown TENGs or with neurons in a three-dimensional matrix (i.e., non-stretched) and/or injecting neurons into the distal nerve segment, wherein the methods provided maintain the pro-regenerative capacity of the distal nerve segment, and wherein the method is used in addition to, or as a complement to, a primary procedure for nerve repair. Exemplary primary procedures for nerve repair include implantation of autografts, allografts, acellular nerve autografts, stretch-grown TENGs, or nerve guidance tubes with or without neurotrophic factors and/or ancillary cells (neurons, Schwann cells, stem cells, and the like) to bridge the nerve lesion or primary nerve injury site. In some embodiments, the methods provided herein ensure that the regenerating axons growing from the proximal end of an injury have a roadmap to appropriate targets in the distal nerve segment by maintaining the efficacy and pro-regenerative capacity of the distal nerve support structure and cells. In some embodiments, the method provided comprises contacting multiple distal nerve segments with one or more stretch-grown TENG. In some embodiments, the method provided comprises contacting multiple distal nerve segments with neurons in a three-dimensional matrix (i.e., non-stretched) and/or injecting neurons.

In some embodiments, the methods provided herein are used in addition to a primary procedure and provide a greater degree of functional recovery following repair of PNI, as compared to the degree of functional recovery that occurs when only the primary procedure is utilized. For example, in one embodiment, functional recovery is increased by about 5%, about 10%, about 20%, about 30%, about 40%, about 50%, about 60%, about 70%, about 80%, about 90%, about 100% or more by the use of the methods provided herein. In some embodiments, the methods provided herein are used in the absence of a primary procedure and provide a greater degree of functional recovery following repair of PNI.

In one embodiment, the methods provided herein may encompass single or multiple procedures to maintain the pro-regenerative capacity of the distal nerve segment over extended time periods (e.g., greater than 6 months). In another embodiment, the methods provided herein may encompass single or multiple procedures to maintain the pro-regenerative capacity of the distal nerve segment until at least such time as proximal nerve axons reinnervate distal targets.

In another embodiment, the methods provided further comprise providing one or more neurotrophic factor to the distal nerve segment. In some embodiments, methods are provided for maintaining a distal nerve segment subsequent to a nerve injury in a subject, and the method further comprises administering one or more neurotrophic factor to the subject. In one embodiment, the method further comprises providing culture supernatants derived from nerve cell cultures, TENG cultures, or other cultures that may comprise neurotrophic factors, or that may comprise other factors that may maintain the pro-regenerative capacity of the distal nerve segment. In one embodiment, the neurotrophic factor or culture supernatant comprising a neurotrophic factor may be administered by intra-nerve, intravenous, intraperitoneal, intracerebral, intramuscular, intraocular, intraarterial, intralesional, or topical routes. In another embodiment, the neurotrophic factor or culture supernatant comprising a neurotrophic factor may be administered directly or via a nerve cuff. In one embodiment, a method is provided for maintaining the pro-regenerative capacity of Schwann cells. In another embodiment a method is provided for enhancing survival of Schwann cells. In another embodiment, the method does not comprise transecting a nearby healthy nerve and/or the repaired nerve.

BRIEF DESCRIPTION OF THE FIGURES

FIGS. 2A-2B, shows a representative CNAP measurement (FIG. 2A) and results from the angle board model of functional restoration after TENG implantation in a rat sciatic nerve injury model (FIG. 2B).

FIG. 3, comprising FIGS. 3A-3C, shows CNAP (mV) versus time in rats 10 weeks after receiving TENG or autograft transplants at the site of sciatic nerve lesions. FIGS. 3A and 3B show 1400-1600 µA stimulation of TENG and autograft groups, respectively; FIG. 3C shows a 2000 µA stimulation from the TENG group.

FIG. 4, comprising

FIG. 11, comprising FIG. 11 also shows a method to measure the regeneration of axons at the regenerative front (A1) and pioneer axons (A2), and Schwann cell penetration across the graft.

FIG. 12, comprising

FIG. 14, comprising

FIG. 18, comprising

DETAILED DESCRIPTION OF THE INVENTION

Figure 1:
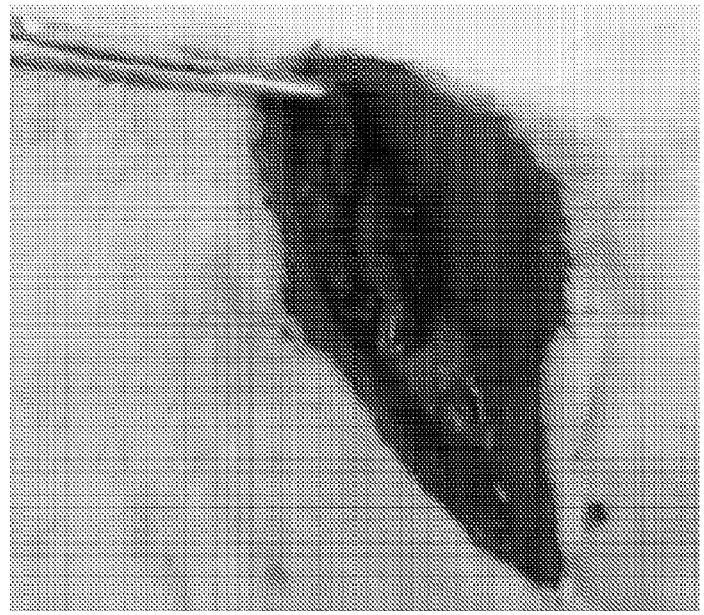
FIG. 1 is a set of images showing a TENG surgically implanted into a rat sciatic nerve lesion (left panel) and the regenerated nerve 16 weeks after surgical implantation (right panel).
Figure 1:
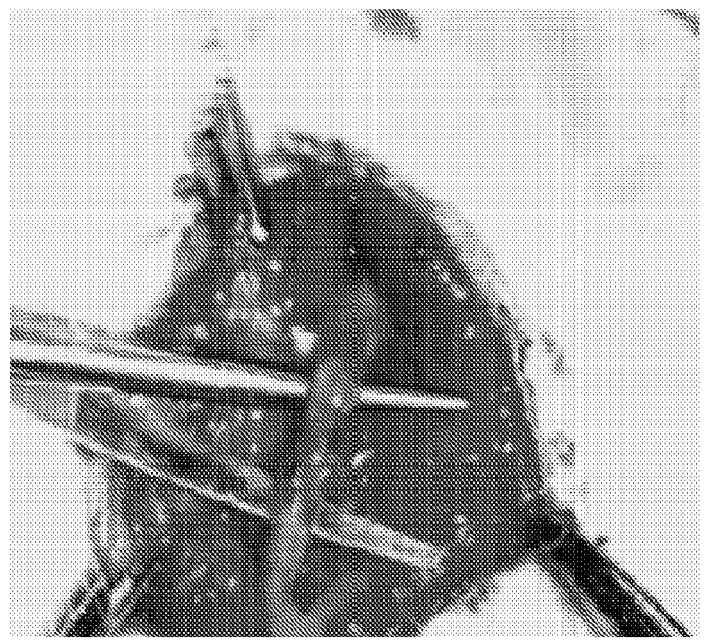

In one aspect of the present invention, tissue engineered nerve grafts (TENGs) or neurons (e.g., neurons in media, suspension or within a three-dimensional matrix) are transplanted to the distal nerve structure, at or away from the primary lesion site, closer to the end target to "babysit" the distal pathway. TENGs or neurons transplanted onto or into the denervated distal nerve will extend axons and/or produce neurotrophic factors to maintain/prolong the pro-regenerative environment of the distal nerve structure, which will facilitate and guide axon regeneration to an appropriate target. In one embodiment, TENGs or neurons transplanted at the end of, onto, or into the denervated nerve will lead resident Schwann cells in the distal sheath to maintain their pro-regenerative phenotype and alignment over extended time periods. In another embodiment, TENG or neuron transplants will also improve resident Schwann cell survival, preventing the cells from degenerating. Thus, TENG or neuron transplants, in some embodiments, create a suitable environment for axon regeneration by maintaining the efficacy of the distal pathway to provide a guide for regenerating host axons to reach and innervate long-distance targets.

In one embodiment, the methods provided herein are secondary methods to be used in conjunction with a primary procedure for nerve lesion repair. Primary procedures, include, but are not limited to, implantation of autografts, allografts, acellular nerve allografts, stretch-grown TENGs, or nerve guidance tubes (with or without neurons) at the proximal end of the nerve injury. In some embodiments, the methods provided herein are used in addition to, or as a complement to, the primary procedure. In some embodiments, the methods provided herein ensure that the regenerating axons provided by the primary procedure have a roadmap to appropriate targets in the distal nerve segment by maintaining the efficacy of the distal nerve support structure and cells. In some embodiments, the methods provided herein are used in addition to a primary procedure (e.g., nerve guidance tube, autograft, or stretch-grown TENG transplant) and provide a greater degree of functional recovery following repair of PNI, as compared to the degree of functional recovery that occurs when only the primary procedure is utilized. In some embodiments, the methods provided herein provide a more complete degree of functional recovery following repair of PNI, as compared to the degree of functional recover that occurs when only the primary procedure is utilized. For example, in one embodiment, functional recovery is increased by 5%, 10%, 20%, 30%, 40%, 50%, 60%, 70%, 80%, 90%, 100% or more by the use of the methods provided herein. In some embodiments, the methods provided herein are used in the absence of a primary procedure and provide a greater degree of functional recovery following PNI. In some embodiments, the methods provided herein provide a more complete degree of functional recovery following PNI, as compared to the degree of functional recover that without treatment. For example, in one embodiment, functional recovery is increased by 5%, 10%, 20%, 30%, 40%, 50%, 60%, 70%, 80%, 90%, 100% or more by the use of the methods provided herein The neurons useful in the methods provided herein include all neuronal subtypes (PNS motor or sensory, CNS, or iPCS/stems cells differentiated into a neuronal phenotype), and may be delivered to the distal nerve by implantation (e.g. a stretch-grown TENG or neurons in a three-dimensional matrix may be implanted into or in the vicinity of the distal nerve structure) or directly injected into the distal nerve structure (e.g., neurons may be directly injected into the nerve fascicles at the distal nerve structure). In one embodiment of the present invention, neurons are derived from any cell that is a neuronal cell (e.g., cortical neurons, dorsal root ganglion neurons or sympathetic ganglion neurons) or is capable of differentiating into a neuronal cell (e.g., stem cell). Neurons useful in the invention may be derived from cell lines or other mammalian sources, such as donors or volunteers. In one embodiment, the neurons are human neurons. In one embodiment, the neurons are non-human mammalian neurons. In one embodiment, the neurons are dorsal root ganglion neurons or sympathetic ganglion neurons. In another embodiment, neurons are derived from immortalized cell lines that are induced to become neuron-like (e.g. NT2, PC12). In a further embodiment, the neurons are human dorsal root ganglion neurons or human ganglion sympathetic neurons. In one embodiment, the neurons are human dorsal root ganglion neurons obtained from a cadaver. In another embodiment, the neurons are human dorsal root ganglion neurons obtained from patients who have undergone ganglionectomies. Alternatively, sympathetic ganglion neurons are obtained from a cadaver or through endoscopic extraction from a subject. Furthermore, the neurons may be singular, integrated neurons or a plurality of integrated neurons (i.e., an integrated nerve bundle). Optionally, the neuron is genetically modified. For instance, neurons may be modified to express a neurotrophic factor. In some embodiments, expression of a neurotrophic factor is transient. Methods of genetically modifying neurons, such as viral transduction/transfection and electroporation, are well known to the skilled artisan.

In a further embodiment, the stretch-grown TENG, including the elongated fascicular axon tracts, is coated, embedded, and/or encased in a biocompatible matrix. In one embodiment, the elongated neurons are encased in a biocompatible matrix immediately after completion of the elongation process. In another embodiment, the biocompatible matrix is present during the elongation process. In another embodiment, the elongated neurons are encased immediately prior to transplantation. In another embodiment, the TENG is essentially surrounded by a sheet of a biocompatible material to form a sheath. Such a composition may be prepared, for instance, by placing a sheet of biocompatible material on the bottom of the elongator apparatus and stretch-growing axons over it. The stretch-grown neurons may then be coated with the biocompatible matrix prior to removal from the elongator frame, and the sheet of biocompatible material, with the elongated neurons and biocompatible matrix, are removed from the elongator frame. The elongated neurons and matrix are then surrounded by the sheet of biocompatible material, for instance, by bringing two edges of the sheet together to form a cylinder, thus forming a sheath. The skilled artisan, armed with the instant disclosure, will recognize other methods of assembling the TENG composition useful in the methods of the invention. In one embodiment, the elongated neurons are elongated to at least about 10 mm. In one embodiment, the elongated neurons are elongated to at least about 1 cm. In another embodiment, the elongated neurons are elongated to at least about 3 cm. In another embodiment, the elongated neurons are elongated to at least about 5 cm.

In one embodiment, TENGs are transplanted to the distal nerve segment. In a further embodiment, a section of the distal nerve sheath is removed, and the TENG is placed in the position previously occupied by the portion of the distal nerve that was removed. In one embodiment, the entirety of the TENG or a portion of the TENG occupies the position previously occupied by the portion of the distal nerve that was removed. In one embodiment, neurons are injected directly into the distal nerve segment. In a further embodiment, neurons are contained within or injected directly into nerve fascicles. In another embodiment, neurons are injected into a conduit or device that directly interfaces with the distal nerve segment. In one embodiment, the conduit or device that directly interfaces with the distal nerve sheet may be a nerve guidance tube.

In one embodiment, TENGs are directly placed into the distal nerve environment without encasement. Thus, in one embodiment, the distal nerve segment is opened longitudinally, a TENG is placed in the distal nerve segment, and the distal nerve segment is closed around the TENG via suture or other means.

In the presence of a nerve injury, Schwann cells lose contact with axons and, in response, lose their differentiated morphology and myelinating phenotype, downregulate genes related to myelin, and upregulate genes involved in axon growth and neuronal survival. Schwann cells in this state proliferate, when necessary, and transform morphologically into cells capable of forming long regenerative columns. The cells form regenerative columns for regenerating axons, guiding them to appropriate targets. Once axons have regenerated, Schwann cells transform again into differentiated myelinating and non-myelinating Schwann cells. Schwann cells with morphology to form long, aligned columns following nerve injury are considered to be "pro-regenerative Schwann cells." Thus, the phrases "pro-regenerative alignment and phenotype of Schwann cells," and "pro-regenerative capacity of Schwann cells," as used herein, refer to an architecture, phenotype, and environment of Schwann cells that allows Schwann cell-mediated support of the denervated nerve. In the absence of regenerating axons over time, the pro-regenerative phenotype of Schwann cells fails, eventually leading to the death of Schwann cells and the degradation of the entire distal nerve segment (i.e. loss of epineurium, perineurium, endoneurium and all associated supporting vasculature, cells, extracellular-matrix, etc.).

It is contemplated that the methods of the present invention will be applicable to maintaining the pro-regenerative capacity of the distal nerve segment for subjects with spinal cord injury as well as other nerve lesions, such as those derived from a neurodegenerative disease (e.g., including ALS and Parkinson's disease) or peripheral neuropathy. The term "peripheral neuropathy" refers to damage to the peripheral nerve system that is caused by an inherited disease, physical trauma, tumor, toxin, infection, autoimmune response, nutritional deficiency, vascular disorder, or metabolic disorder. Diseases or infectious organisms that may cause peripheral neuropathy include, but are not limited to, acute inflammatory demyelinating neuropathy, Guillain-Barré syndrome, chronic inflammatory demyelinating polyneuropathy (CIDP), Charcot-Marie-Tooth disease, amyloid polyneuropathy, multifocal motor neuropathy, Lyme disease, diptheria, leprosy, human immunodeficiency virus (HIV), herpes varicella-zoster, Epstein-Barr, cytomegalovirus, and herpes simplex viruses. The compositions and methods of the invention may also be used to restore communications of a severed limb, organ or tissue with the central nervous system. Nerve injuries that may be treated using the methods of the present invention include lesions in the central nervous system (CNS) and/or in the peripheral nervous system (PNS). The CNS includes the brain, spinal cord, optic, olfactory and auditory systems. The PNS includes neurons and nervous tissue that reside or extend outside of the CNS. In one embodiment, the lesion is a spinal cord injury. In another embodiment, the lesion is an optic nerve lesion. In another embodiment, the lesion is any peripheral nerve lesion, including upper and lower limb, genitourinary nerve and craniofacial nerve damage.

The methods provided may be used with any subject having or suspected of having a nerve injury. In one embodiment, the subject is a mammal. In a further embodiment, the subject is a veterinary animal, such as, but not limited to, non-human primates, horses, cattle, sheep, dogs, cats, pigs, and goats. In another embodiment, the subject is a human.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

As used herein, the term "babysit" or "babysitting" refers to the function of a composition, method, process, or procedure for maintaining the pro-regenerative capacity of the distal nerve segment following a nerve injury. In one embodiment, the Schwann cells in the distal nerve segment are maintained in a pro-regenerative phenotype and alignment by compositions or methods that serve to babysit the distal nerve segment. In another embodiment, the compositions and methods that serve to babysit the distal nerve segment enhance the survival of Schwann cells. In another embodiment, the pro-regenerative capacity of the distal nerve segment is maintained until at least such time as proximal nerve axons reinnervate distal targets The term "neuron" is used interchangeably herein with the term "neuronal cell. As used herein, a "nerve construct" refers to composition comprising at least one neuron. As used herein, "elongated neuron" is used interchangeably with "stretch-grown neuron" and refers to a neuron that has had the axon increase in length as a result of an ex vivo stretching procedure compared to a comparable neuron that has not been subjected to the ex vivo stretching procedure.

An elongated neuron comprises a cell body and at least one elongated axon. The at least one elongated neuron possesses an elongated axon that spans a distance and is connected to another cell, preferably another neuron and more preferably, another elongated neuron. Exemplary stretching procedures are described in U.S. Pat. No. 6,365,153. In some embodiments, the elongated neuron is a mechanically elongated neuron.

As used herein, the term "tissue-engineered nerve graft (TENG)" refers to a transplantable nerve construct or nerve tissue that is generated in culture. "TENG" is used interchangeably herein with the term "stretch-grown TENG." More specifically, TENGs are elongated, or stretch-grown, axons and neurons in a three-dimensional matrix. Thus, in one embodiment, TENGs are elongated neurons, which comprise long integrated axonal tracts spanning two populations of neurons. In one embodiment, TENGs are generated via the stretch growth process described in U.S. Pat. No. 6,365,153, which is incorporated herein by reference in its entirety. In some embodiments, the elongated neuron is a mechanically elongated neuron or any method that produces elongated tracts of axons. Following mechanical elongation of neurons to produce stretch-grown axons, the cultures can be embedded in a three-dimensional matrix for removal from the culture environment, thus creating "stretch-grown TENGs." As used herein, TENGs are distinct from "neurons in a three-dimensional matrix," which are not stretch-grown or elongated. In one embodiment, stretch-grown TENGs are transplanted, or connected, to the distal nerve structure following nerve injury and serve to maintain the pro-regenerative capacity of the environment of the denervated distal nerve. In another embodiment, neurons in a three-dimensional matrix or in suspension are transplanted to the distal nerve via direct injection into the nerve structure following nerve injury, and serve to maintain the pro-regenerative capacity of the environment of the distal nerve structure. In one embodiment, tens of neurons, thousands of neurons, millions of neurons, tens of millions of neurons, or more are injected. In a further embodiment, multiple direct deliveries and/or injections of neurons are conducted over time. In one embodiment, neuron injections are conducted quarterly, bi-annually, annually, or according to various regimens until the nerve injury has been sufficiently treated.

As used herein, "biocompatible" refers to a material that is substantially non-toxic to neuronal cell bodies and axons and that is substantially non-toxic to the cells and tissues of a recipient of the composition. A biocompatible material, when introduced into an individual, is not toxic or injurious to that individual, nor does it induce immunological rejection of the material in the mammal.

As used herein, "synapse" refers to a junction between a neuron and another cell, across which chemical communication flows. As used herein, "synapsed" refers to a neuron that has formed one or more synapses with one or more cells, such as another neuron or a muscle cell. As used herein, "synaptically integrate" refers to the formation of at least one synapse between a neuron and at least one other cell. The other cell may be a nerve cell, a muscle cell or another neuron target. For instance, two neurons are synaptically integrated if at least one synapse exists between the two cells.

As used herein, a "sheath" refers to a structure intended to support, position and/or hold a nerve in place. Thus, a sheath may provide a means of securing the position of a TENG. In one embodiment, the sheath is intended to hold a nerve construct in place, for instance, in a nerve lesion site. The sheath may be endogenous (e.g., the epineurium or perineurium) or exogenous (e.g., a nerve guidance tube) to the nerve. A sheath at least partially enfolds a nerve or nerve construct. As used herein, "at least partially enfolds" encompasses partial or complete surrounding of part or all of a nerve or nerve construct. It therefore encompasses a completely surrounded nerve or nerve construct. Surrounding a nerve or nerve construct means at least one neuron is surrounded by a sheath. In some embodiments, the neuron is all or a part of a stretch-grown nerve construct. In some embodiments, the sheath is a synthetic sheath. Preferably, the synthetic sheath is flexible and can be sutured. Optionally, the sheath is bio-resorbable or biodegradeable.

As used herein, "proximal" refers to a position that is nearer to the spinal cord or brain as compared to another or other positions. As used herein, "distal" refers to a position that is some distance from the primary injury site. The distal position is farther away on the nerve path as compared to the proximal position. The distance between the distal position and the injury site can be any distance including 1 mm or smaller, up to one or more meters in length or more. For example, the distance between the distal position and the injury site can be less than 1 cm, at least about 1 cm, at least about 3 cm, at least about 10 cm, at least about 1 meter, or more. Multiple distal sites are also encompassed by the invention. Thus, stretch-grown TENG or neurons in a three-dimensional matrix or in suspension, or both, may be applied to multiple distal sites in a subject. In some embodiments, the proximal or distal position of a nerve injury is referred to as the proximal nerve sheath, stump or structure, or the distal nerve segment, stump or structure, respectively. Thus, in the context of a nerve injury, the terms "distal sheath," "distal stump," and "distal structure," are used interchangeably herein. Similarly, the terms, "proximal sheath," "proximal stump," and "proximal structure" are used interchangeably herein.

In one embodiment, TENGs or neuronal cells may be modified, altered or induced to express one or more neurotrophic factor. In another embodiment, TENG or neuron transplants may be administered in conjunction with one or more neurotrophic factors. In another embodiment, TENG or neuron transplants may be administered in combination with culture supernatants derived from nerve cell cultures, TENG cultures, or other cultures that may comprise neurotrophic factors; or may be administered in combination with other factors, including cells, proteins, peptides, nucleic acids and/or drugs, that may enhance or maintain the pro-regenerative capacity of the distal nerve segment. In one embodiment, one or more of these factors may be administered by intra-nerve, intravenous, intraperitoneal, intracerebral, intramuscular, intraocular, intraarterial, intralesional, or topical routes. In another embodiment, one or more of these factors may be administered directly or via a nerve cuff. As used herein, a "neurotrophic factor" is a biological, recombinant or synthetic molecule that contributes to the growth and survival of neurons during development, and/or for maintaining adult neurons. Exemplary neurotrophic factors include, but are not limited to, neurotrophin (including, for example, neurotrophin 3 (NT-3), neurotrophin 4/5 (NT-4/5), neurotrophin 6 (NT-6), and neurotrophin 7 (NT-7)), ciliary neurotrophic factor (CNTF), brain-derived neurotrophic factor (BDNF), nerve growth factor (NGF), basic fibroblastic growth factor (bFGF), glial cell line-derived neurotrophic factor (GDNF), neurturin, artemin, persephin, purpurin, transforming growth factor-beta (TGF-beta), and synthetic neurotrophins, such as pan-neurotrophin-1 (PNT-1).

As used herein, a "therapeutic treatment" is a treatment administered to a subject for the purpose of treating, curing, preventing, or diminishing or eliminating one or more symptoms of a disease, defect, disorder or condition. As used herein, a "therapeutically effective amount" is the amount of a composition of the invention sufficient to provide a beneficial effect to the individual to whom the composition is administered. As used herein, "treating a nerve lesion" is used interchangeably with "treating a nerve injury" and means repairing the injured nerve region or reducing the frequency and/or the severity of a symptom of the nerve lesion. As used herein, "nerve injury" is used As used herein, the term "nerve injury" and "nerve lesion" are used interchangeably and refer to any damage or disruption of the neuronal axons.

"Transplant," as used herein, refers to making contact between, or connecting, an exogenous cell or tissue and a host cell or tissue. In the context of TENGs, by "transplant" is meant implantation of the TENG at the desired site. In the context of neurons that do not comprise a TENG, by "transplant" is meant administration of neurons to the desired site, for example, by injection. For example, neurons may be injected directly into the distal nerve segment or into one or more conduits/devices that directly interface with the distal sheath. In one embodiment, the TENG or neuron is transplanted to the site of a nerve injury. In another embodiment, the TENG or neuron is transplanted to the distal nerve structure. In another embodiment, the TENG comprises stretch-grown axons. Methods for transplantation are known to those of skill in the art of cell transplantation. See, for instance, U.S. Pat. No. 6,365,153, incorporated by reference herein in its entirety. Suitable transplant material may be evaluated by using well-known electrophysiological and fluorescence techniques. In one embodiment, transplantation of a TENG involves removing a portion of a nerve at the site of transplant and placing the TENG at the site. In another embodiment, the TENG comprises a bioresorbable sheath that is sutured to tissue site of transplant in order to secure the position of the TENG. In the methods provided herein, the TENG may comprise mechanically elongated neurons from the intended recipient (autologous transplantation), from a genetically identical donor (syngeneic transplantation) or from a non-genetically identical donor (allogeneic or xenogeneic transplantation). In another embodiment, transplantation of neurons involves injecting neurons into the distal nerve segment.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent based on the context in which it is used.

As used herein, "in vitro" and "ex vivo" are used interchangeably to refer to conditions outside the body of a living organism. Thus, in vitro culturing and ex vivo culturing both refer to culturing outside the body of a living organism.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

It will be understood that the invention as disclosed herein is operable in many various embodiments, both those disclosed herein and those not explicitly set forth. The skilled artisan, when armed with the present disclosure, will understand the manifold embodiments included within the scope and spirit of the invention, and that such embodiments are equally part of the invention disclosed herein.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1. Maintenance of Distal Nerves with TENG Transplants

A study was conducted to assess the ability of stretch-grown TENGs to mediate regeneration of axons over a lesion and maintenance of distal nerve segment in the rat sciatic nerve injury model of PNI. TENGs derived from rats were generated via stretch growth. Following stretch growth, TENGs were stabilized in hydrogel and rolled into a nerve guidance tube according to methods known in the art (see, for example, Smith et al. 2009, Progress in Neurobiology 89: 231 and U.S. Patent Application Publication No. US 2006/0292187). In this model, the sciatic nerve of the rat was exposed and a 1.25 cm to 1.5 cm lesion was generated. TENGs in nerve guidance tubes were immediately surgically implanted into the nerve lesion (FIG. 1, left panel). Sixteen weeks after surgical implantation, the nerve guidance tube had degraded and the nerve had regenerated (FIG. 1, right panel).

Figure 2:
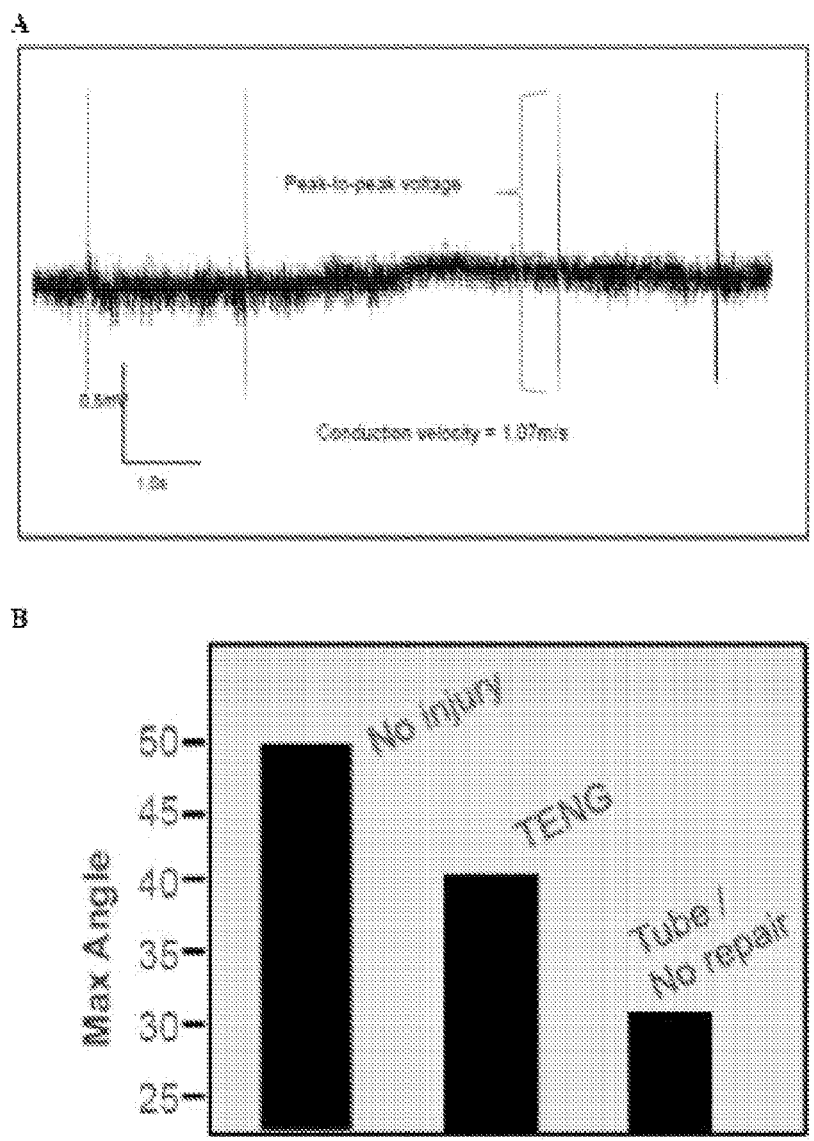
FIG. 2, comprising

In order to measure the restoration of electrophysiology in this model, compound nerve action potential (CNAP) was measured by exposing the sciatic nerve, placing a stimulating electrode 2 mm proximal to the transection site, and placing a recording cuff w 2 mm distal to the graft (FIG. 2A). In addition, to measure restoration of function, an angle board model was employed. In this model, an inclined plane was adjusted to provide a slope of varying grade in order to determine the maximum plane angle at which the animal can maintain position without falling. As shown in FIG. 2B, animals that had received TENGs exhibited superior restoration of function at 16 weeks post TENG implantation in comparison to animals that received either no repair or a nerve growth tube in the absence of TENGs.

Figure 3B:
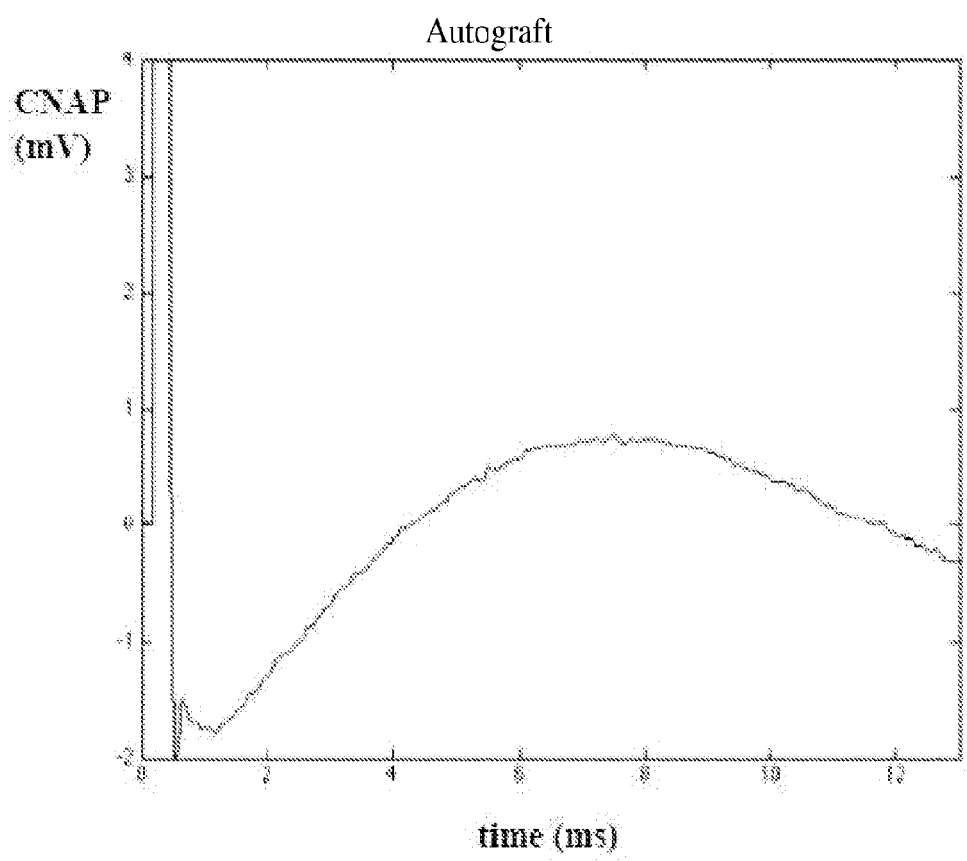
Figure 3C:
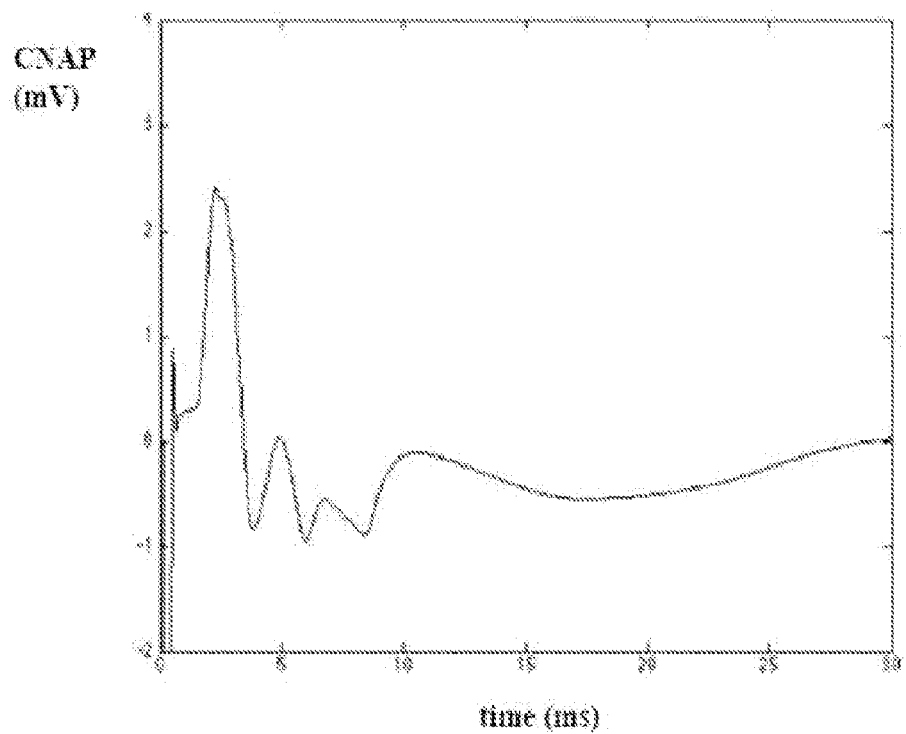
Figure 4A:
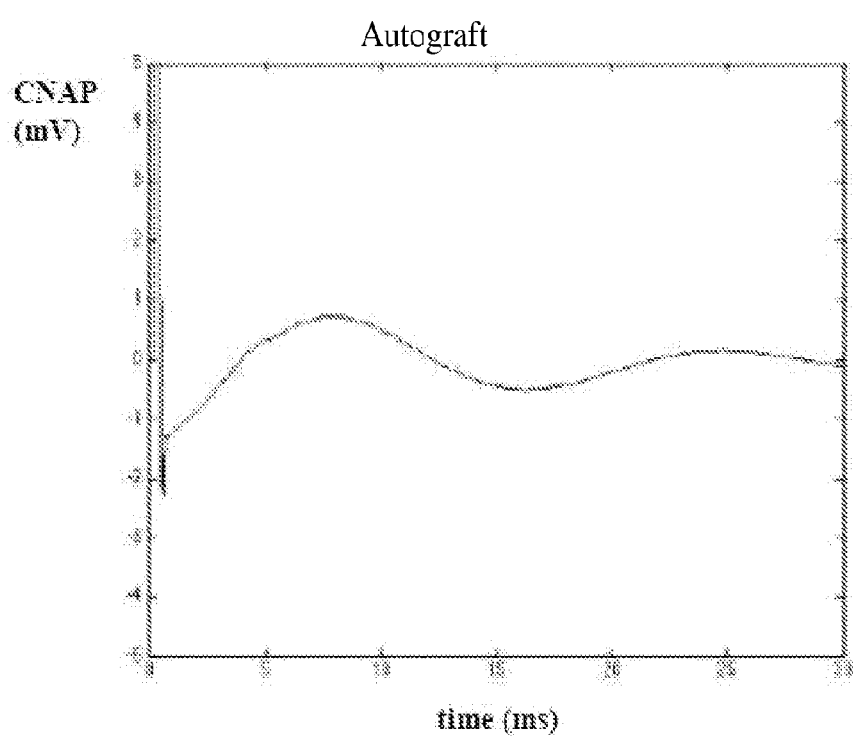
FIGS. 4A-4B, shows CNAP (mV) versus time in rats 12 weeks after receiving TENG or autograft transplants at the site of sciatic nerve lesions (800 µA stimulation).
Figure 4B:
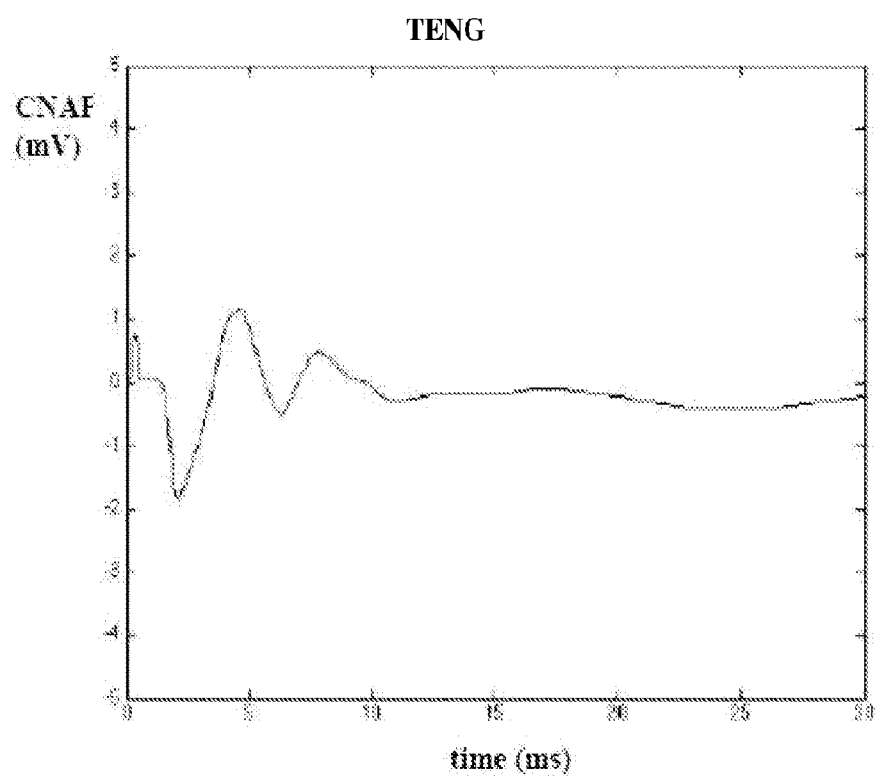
Figure 5:
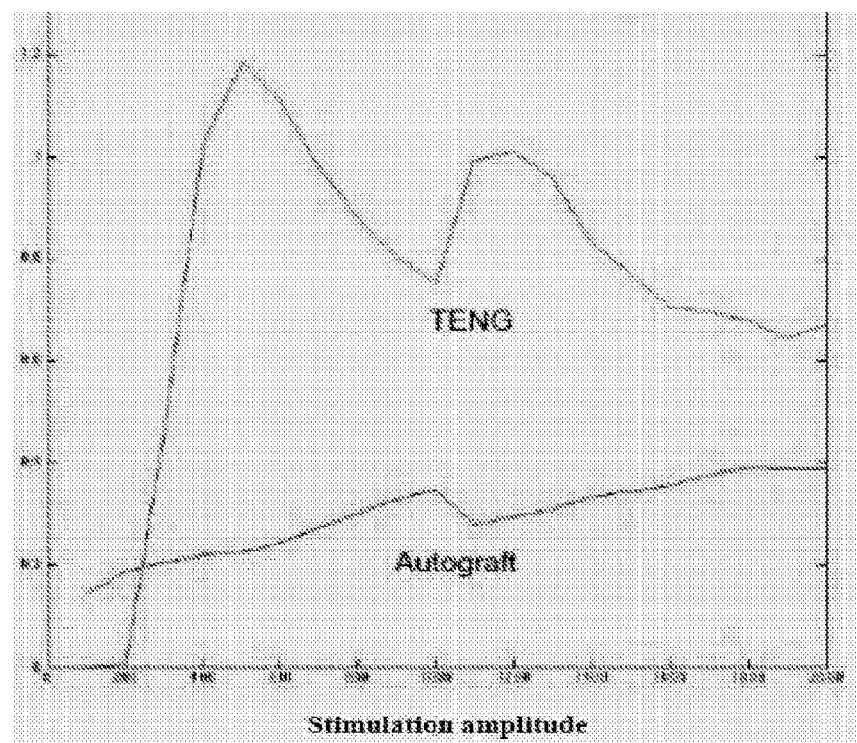
FIG. 5 shows the CNAP measured as the ratio of the ipsilateral to contralateral (naïve) nerve as a function of stimulation amplitude 12 weeks after implantation of TENG or autograft transplants at the site of sciatic nerve lesions.

As early as 10 weeks after surgical implantation of TENGs to bridge a 2 cm lesion site in the sciatic nerve, sciatic nerve stimulation evoked a muscle/foot twitch response and a robust CNAP (FIG. 3). Muscle/twitch was also present at 10 weeks after surgical implantation of autografts, and with a weaker CNAP (FIG. 3). At 12 weeks post repair, TENG groups exhibited enhanced CNAP as compared to autograft groups, which exhibited minimal CNAP at this time point (FIG. 4). Notably, CNAP traces were fundamentally different between nerves repaired with TENGs versus autografts, indicating that there are differences in axon regeneration. As shown in FIG. 5, 12 weeks post-repair of the 2.0 cm lesion, CNAPs were measured for a range of stimulation amplitudes and normalized per animal based on measurements from the contralateral, naïve nerve. In this example, repair with TENGs resulted in a greater CNAP as a function of stimulation amplitude.

Figure 6:
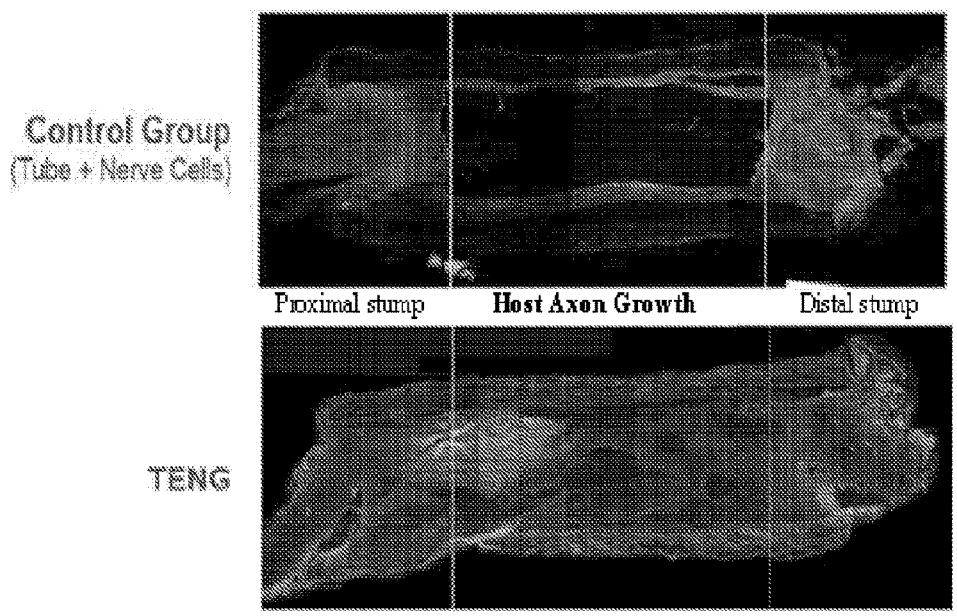
FIG. 6 shows host axon growth (GFP+ axons) at four weeks post implantation of TENG (bottom panels) or NGT with nerve cells (top panels) at the site of sciatic nerve lesion.

A similar study was undertaken with GFP transgenic host rats. In this study, 1.0 cm lesions were generated in the sciatic nerves of GFP transgenic rats. TENGs were implanted at the lesion site. In control GFP rats, nerve guidance tubes containing nerve cells (i.e., non stretch-grown) were implanted at the lesion site. Four weeks after implantation, axon growth at the proximal stump, across the lesion, and at the distal stump was assessed by fluorescence microscopy. As shown in FIG. 6, robust host (GFP+) axon growth was evident in rats that received TENGs, but not control animals. Importantly, axon growth was evident at the distal stump as well as the proximal stump.

Figure 7:
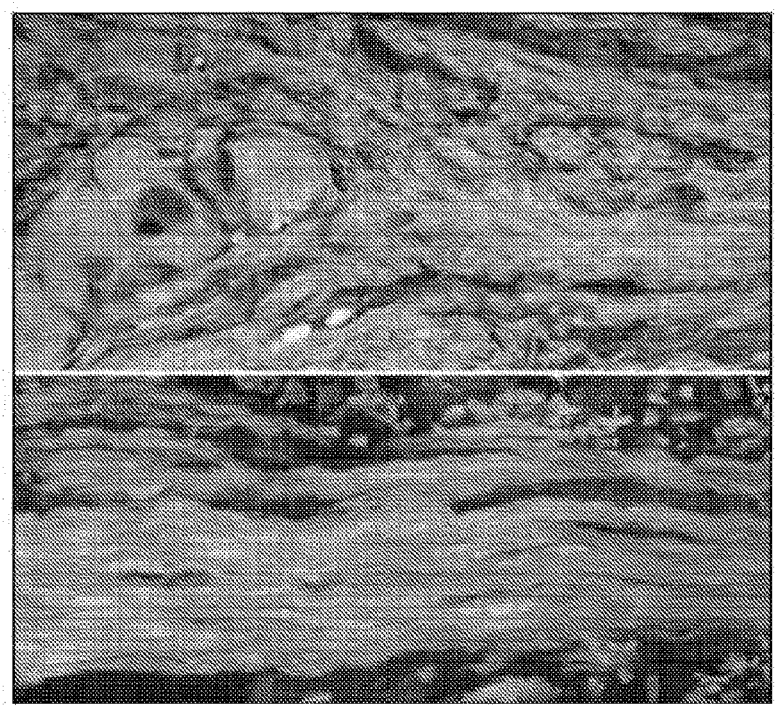
FIG. 7 shows host axons (GFP−) infiltrating across the ganglia of the GFP+ TENGs (top panel), and intimate contact of host axons (GFP−) with GFP+ TENG axons (bottom panel) six weeks after transplant of TENGs to the site of sciatic nerve lesions.
Figure 8:
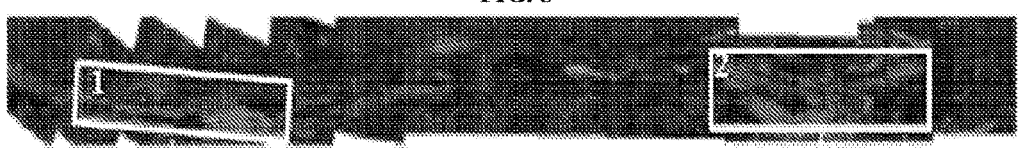
FIG. 8 shows a TENG at 6 weeks post-implant with proximal and distal ganglia spanned by axonal tracts (GFP+; top). Penetration of TENG axons into both the proximal (middle) and distal (bottom) nerve was observed.
Figure 8:
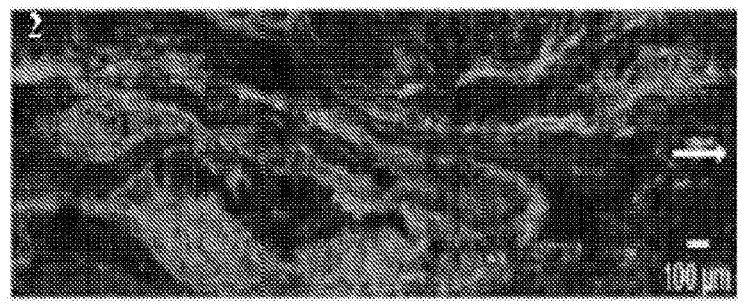
Figure 8:
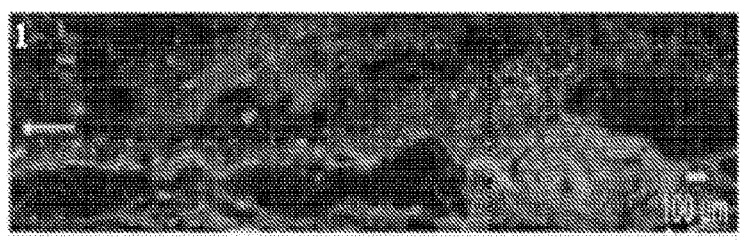
Figure 9:
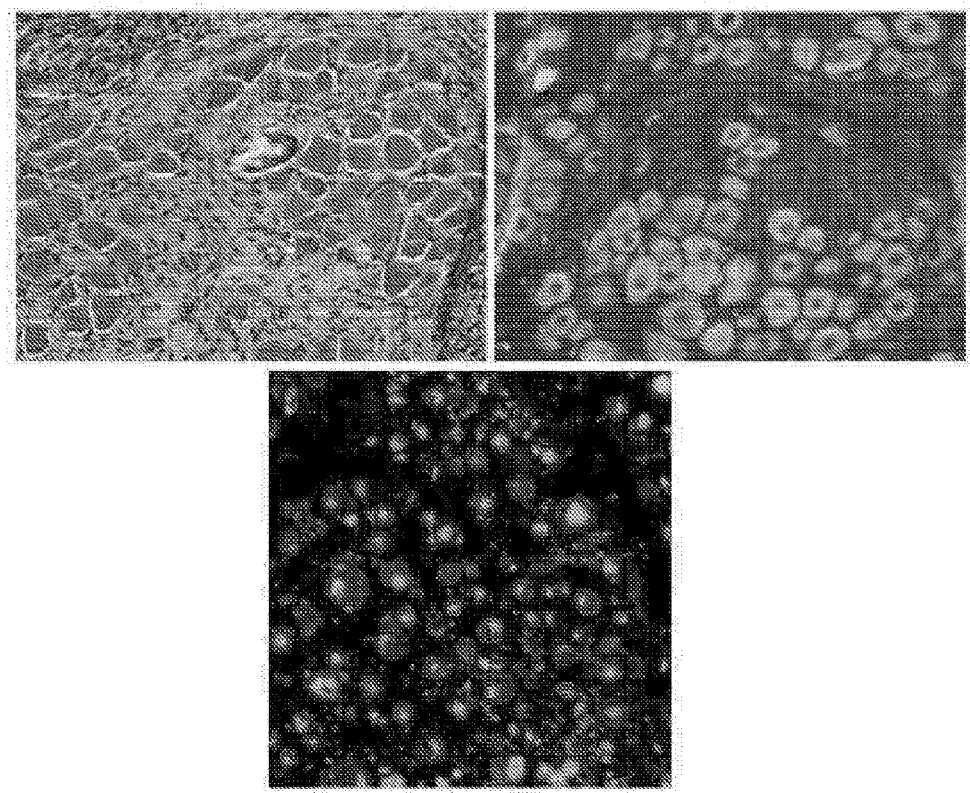
FIG. 9 shows survival of TENG neurons at 4 months post-transplant (top two panels); and myelinated axons at the center of the TENG construct (bottom panel)

In another study, sciatic nerves of non-GFP rats were exposed and 1.2 cm-1.5 cm lesions were generated. TENGs generated from GFP+ rats were implanted at the lesion site. Six weeks post implantation, growth of host axons and intertwining of host axons (neurofilament stained red) with TENG axons (GFP+ TENGs) was observed. As shown in FIG. 7, host axons infiltrated across the ganglia of the TENGs (top panel), and host axons exhibited intimate contact with the axons of TENGs (bottom panel). As shown in FIG. 8, TENGs penetrated into both the proximal and the distal nerve, as both GFP+ and neurofilament+staining was evident. Moreover, long term neuronal survival was shown at 4 months post-transplant by hematoxylin & eosin (FIG. 9, top left panel) and immunostaining for calcitonin and neurofilamant (FIG. 9, top right panel). Also at this time point, axon myelination (FIG. 9, bottom panel) in the graft center was observed, indicating that the host axon infiltration and contact with TENGs was functional and able to lead to axon maturation and recovery of axon function.

Figure 10:
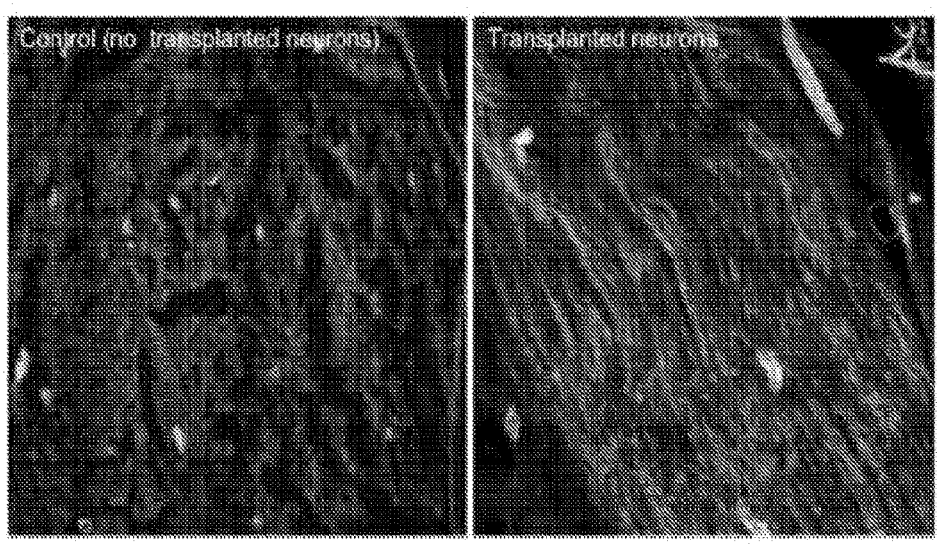
FIG. 10 shows preserved pro-regenerative Schwann cell morphology in the presence of transplanted neurons (right panel), but not in the absence of transplanted neurons (left panel) at 4 months following nerve transection.

In some animals, axon regeneration was prevented by capping the proximal nerve stump after transection. Neurons within a three-dimensional matrix were subsequently transplanted at the end of the distal nerve segment in order to assess the ability of transplanted neurons to babysit the distal pathway. As shown in FIG. 10, right panel, transplanted neurons resulted in maintenance of the nerve micro-structure (green) and Schwann cell morphology (S100 was used to stain Schwann cells, red) associated with a pro-regenerative distal nerve segment at 4 months following nerve transection. In contrast, control (absent transplanted neurons) groups did not exhibit maintenance of the regenerative phenotype of Schwann cells or a pro-regenerative environment in the distal nerve segment at this timepoint (FIG. 10, left panel). The results of the study indicated that transplanted neurons maintained the pro-regenerative capacity of the otherwise denervated peripheral nerve. In particular, transplanted neurons maintained distal nerve segment Schwann cells in their pro-regenerative phenotype and alignment over extended periods of time following nerve transection, indicating that the transplanted neurons were able to "babysit" the distal nerve segment.

Example 2. Acute Repair and Regeneration

A study was conducted to assess the regenerative responses two weeks after implantation of stretch-grown TENGs, autografts, or nerve guidance tubes in a rat sciatic nerve model. Sciatic nerve lesions of 1.0 cm were generated in rats. Sham surgeries or repair with nerve guidance tubes, reverse autografts, or TENGs in nerve guidance tubes were conducted. Reverse autografts are a mixed modality of sensory and motor axons that perfectly match the nerve lesion, which is in contrast to a human autograft, wherein a sensory nerve is used to repair a motor deficit. Nerves were harvested 2 weeks post surgery. Regeneration of host axons was measured by determining the distance or degree of axon regeneration; infiltration of Schwann cells was also measured. Outcome measurements included nerve histology and immunohistochemistry (S100 was used to stain Schwann cells; neurofilament was used to stain axons). In some cohorts, TENG neurons/axons were transduced in vitro to express GFP in order to discriminate host versus TENG axons in vivo.

In these studies, deeply penetrating axons were evident. These deeply penetrating axons reached way out in front of the main group of regenerating axons for autografts. These were termed "pioneer axons," as depicted schematically in FIG. 11A (top panel). Without wishing to be bound by theory, among other potential functions, pioneer axons may act as regenerative scouts, and are able to signal back to the regenerative front and/or condition the distal environment.

Figure 11A:
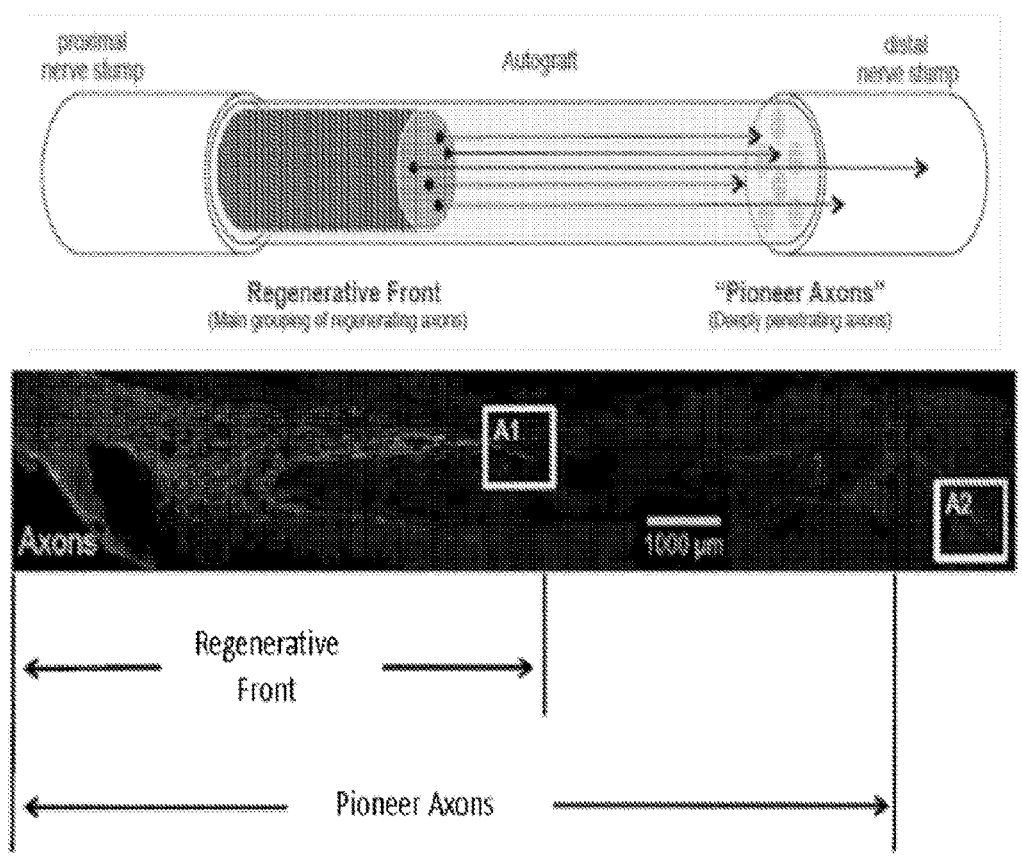
FIGS. 11A-11B, shows a schematic depiction of the regenerative front and pioneer axons (FIG. 11A).
Figure 11B:
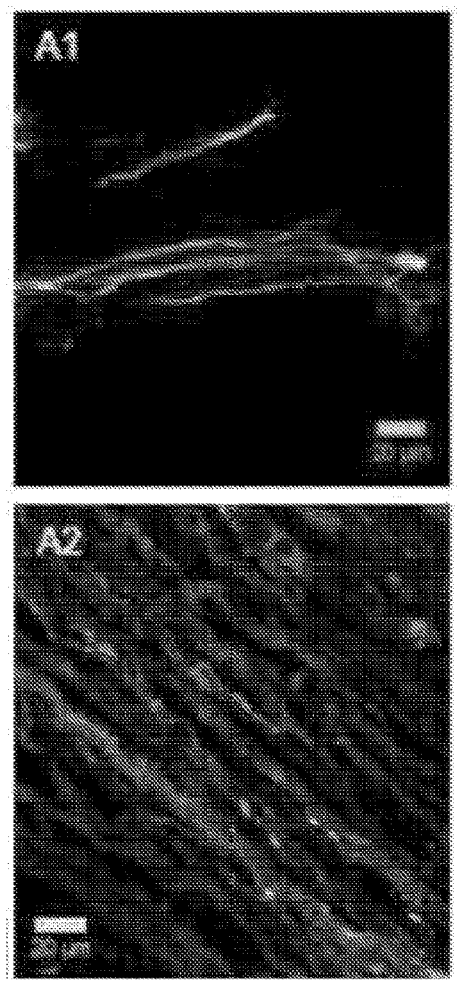
Figure 11B:
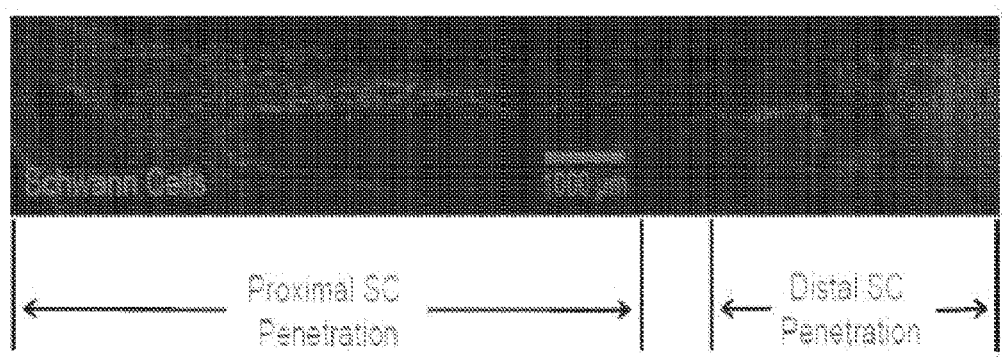
Figure 12A:
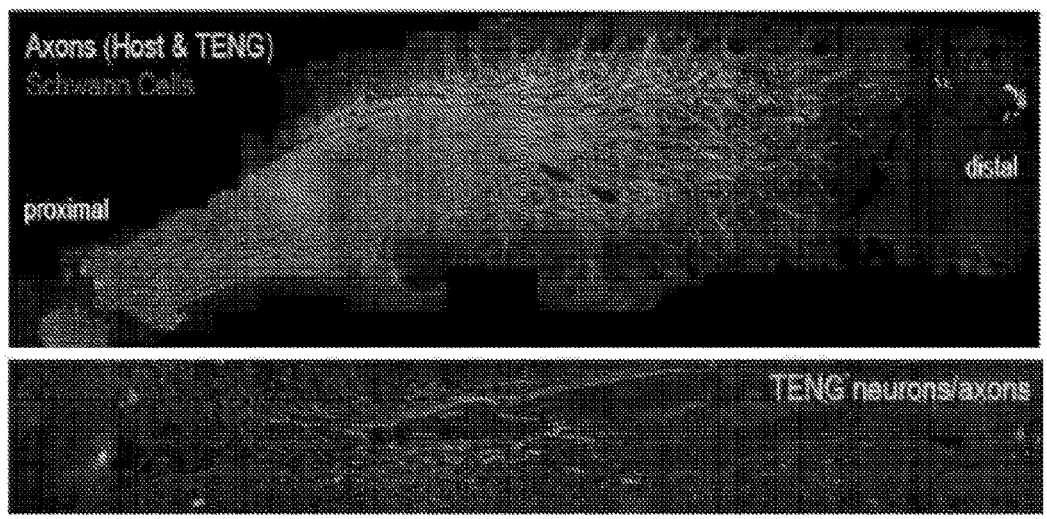
FIGS. 12A-12B, depicts axonal penetration across a TENG (top of FIG. 12A) and neuronal survival and maintenance of axonal architecture in GFP+ TENGs (bottom of FIG. 12A, and FIG. 12B) at two weeks post-implant.
Figure 12B:
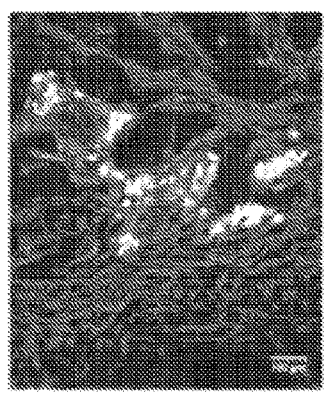
Figure 12B:
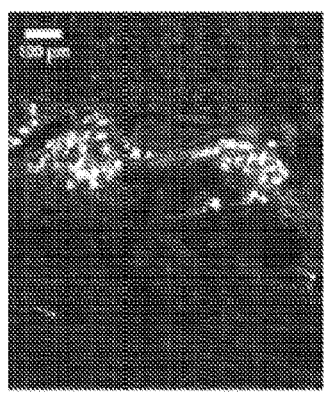
Figure 12B:
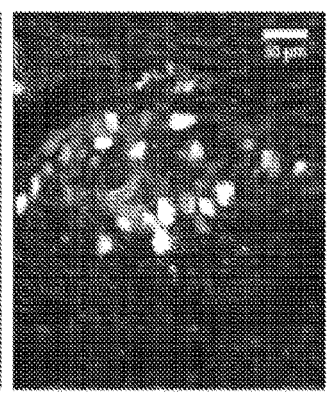
Figure 13:
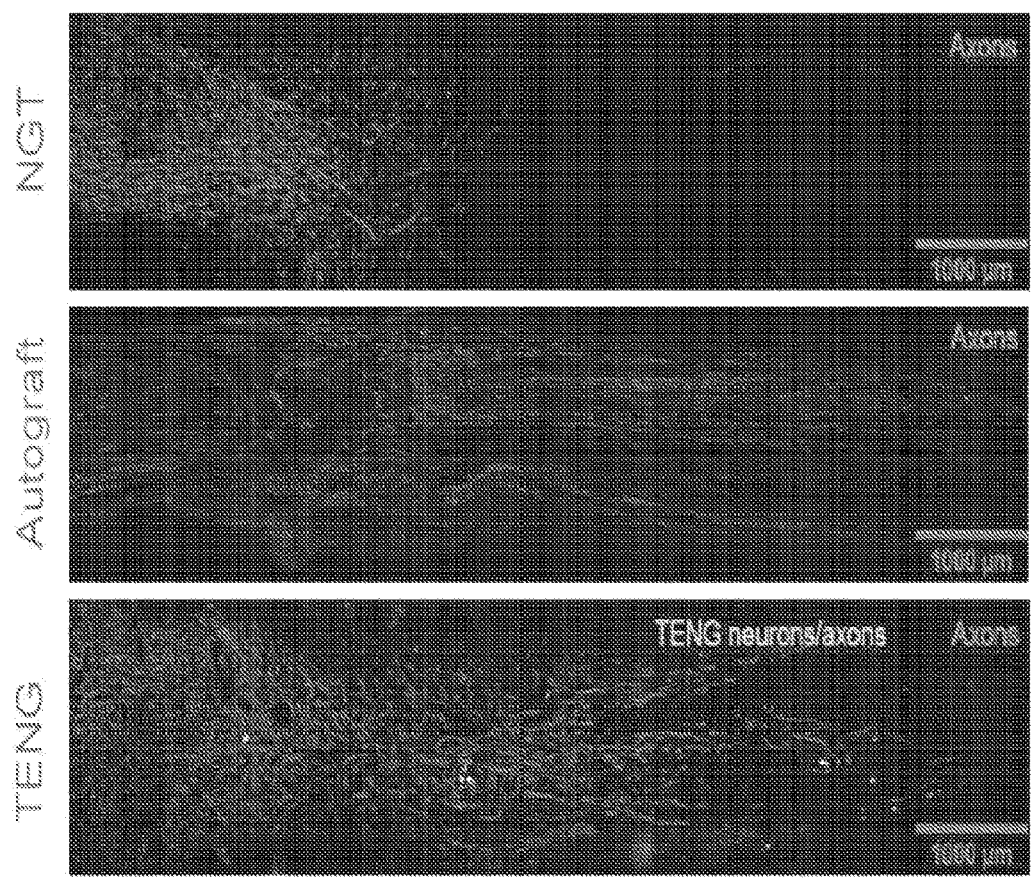
FIG. 13 shows regenerating axons in groups that received TENG implants compared to autograft or NGT groups.

As shown in FIG. 11, axonal regeneration occurred both at the regenerative front and the deeply penetrating axons (i.e., pioneer axons; FIG. 11A). Schwann cell infiltration across the graft was also measured; Schwann cells penetrated both proximal and distal portions of the graft (FIG. 11B). In addition to robust axonal regeneration across the TENGs (FIG. 12A), maintenance of axonal architecture and survival of TENG neurons was also observed (FIG. 12B). TENG neuronal survival and maintenance of axonal architecture also occurred (FIG. 12). Compared to nerve guidance tubes (NGTs) alone, TENGs increased regenerating axonal penetration across the lesion (FIG. 13).

Figure 14A:
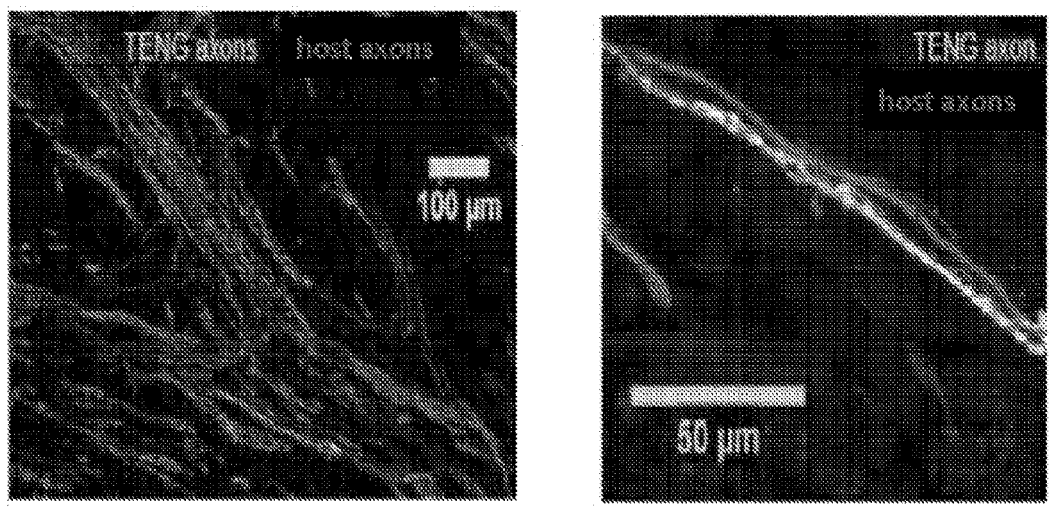
FIGS. 14A-14B, shows host axonal regeneration occurring along the TENG axons. White arrows point to the altered growth direction of host axons when TENGs were placed off-center, versus the proximal stump trajectory (grey arrows).
Figure 14B:
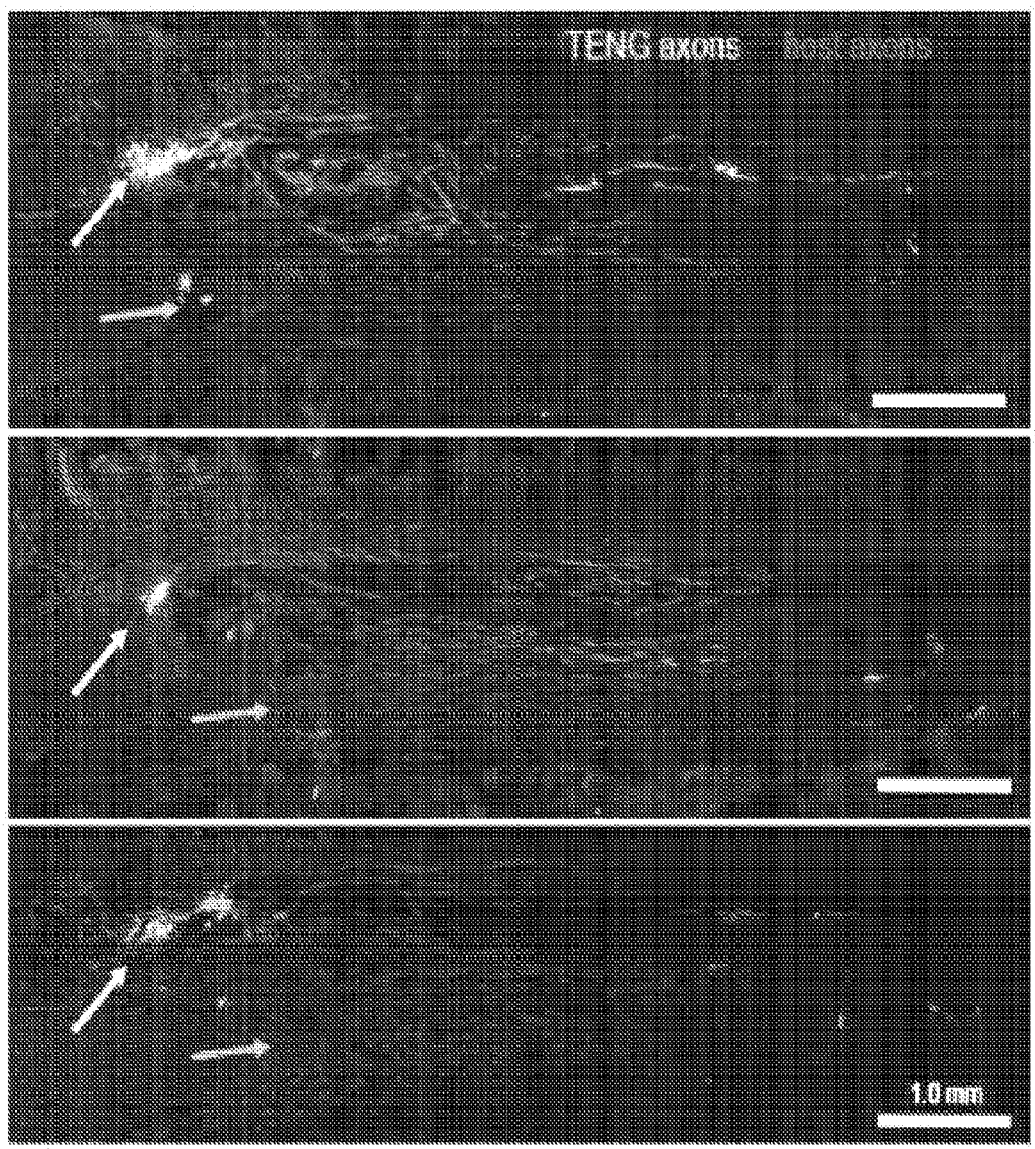

As shown in FIG. 14A, host axonal regeneration in the TENGs often occurred directly along TENG axons. When TENGs were placed off-center, host axons altered their growth direction (see white arrows in FIG. 14B rather than strictly following the proximal stump trajectory (see grey arrows in FIG. 14B). Thus, TENG neurons/axons directed and guided host axon regeneration.

Figure 15:
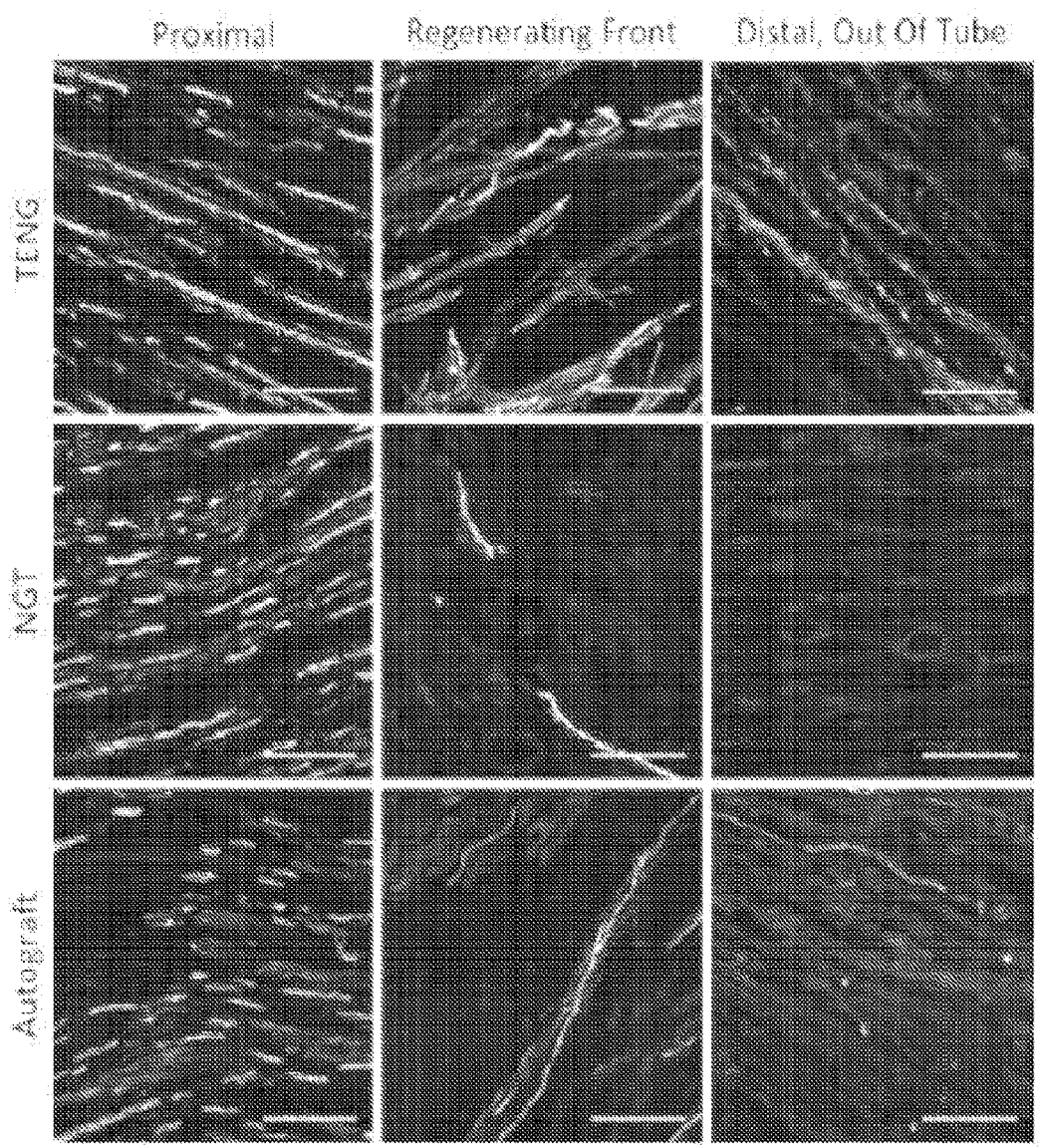
FIG. 15 shows pioneer axons present in the proximal, regenerating front, and distal nerve segment in the TENG and autograft group (top and bottom row, respectively); pioneer axons were not detectable in the distal nerve segment in the NGT group (middle row).

At 2 weeks post-implantation, pioneer axons were observed in the distal nerve segment for the TENG and autograft groups, but not in NGT groups (FIG. 15). In the TENG group, pioneer axons a mix of host axons and TENG axons, with the latter extending the living labeled pathway to further promote regeneration (FIG. 15, top row).

Figure 16:
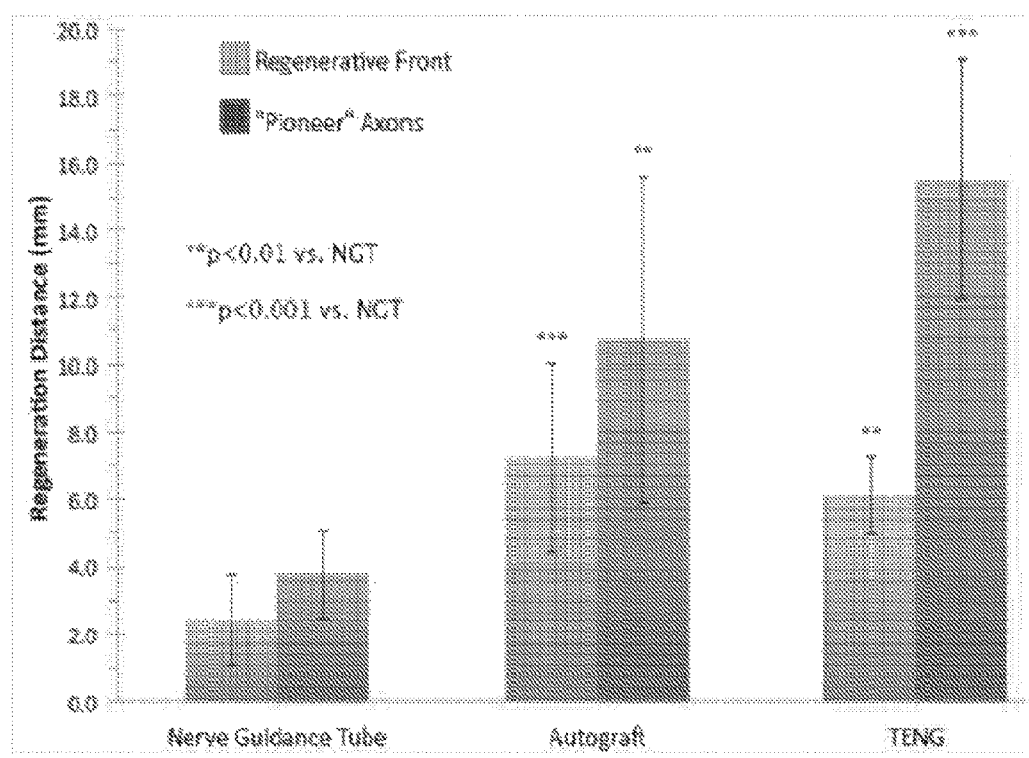
FIG. 16 depicts a quantitative analysis of the regeneration distance of the regenerative front and the pioneer axons in NGTs versus autografts versus TENGs at two weeks post-implant.

The regeneration distance for both regenerative front and pioneer axons in each group was quantified. As shown in FIG. 16, TENGs were statistically equivalent to autografts for the regenerative front ($p=0.59$), with a trend toward enhancing pioneer axon penetration ($p=0.081$). TENGS significantly accelerated axonal regeneration versus NGTs ($p<0.001$). Notably the reverse autografts are distinct from human autografts in that they are a mixed modality of sensory and motor axons that perfectly match the nerve lesion, in contrast to the sensory nerves used to repair a motor deficit in human autografts. Thus, without wishing to be bound by theory, it is expected that axonal regeneration with TENGs would be superior to axonal regeneration with the use of human autografts. Host axonal regeneration with TENGs was four fold faster than host axonal regeneration with NGTs. TENG and autograft host axon growth rates were 0.57 mm/day, whereas NGTs host axon growth rates were 0.14 mm/day.

Figure 17:
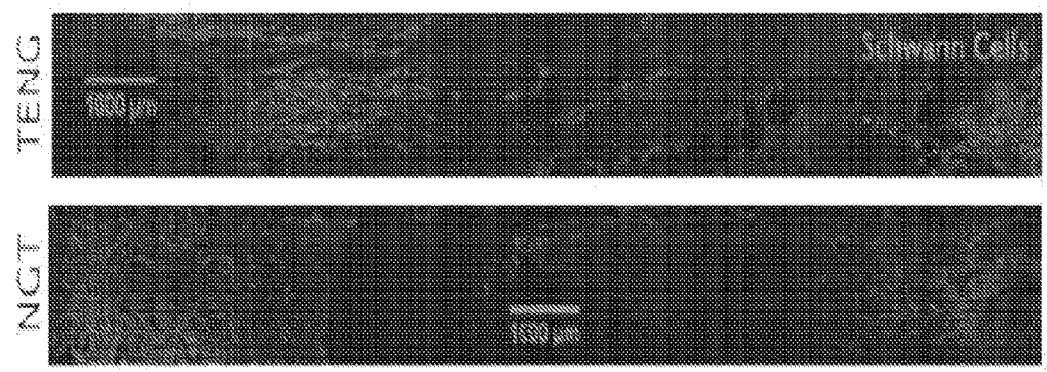
FIG. 17 shows images of reconnection of proximal and distal Schwann cells in TENG but not in NTG groups (top two panels); and a quantitative analysis of the infiltration distance into the nerve gap in TENGs versus NGTs (bar graph) at two weeks post-implant.
Figure 17:
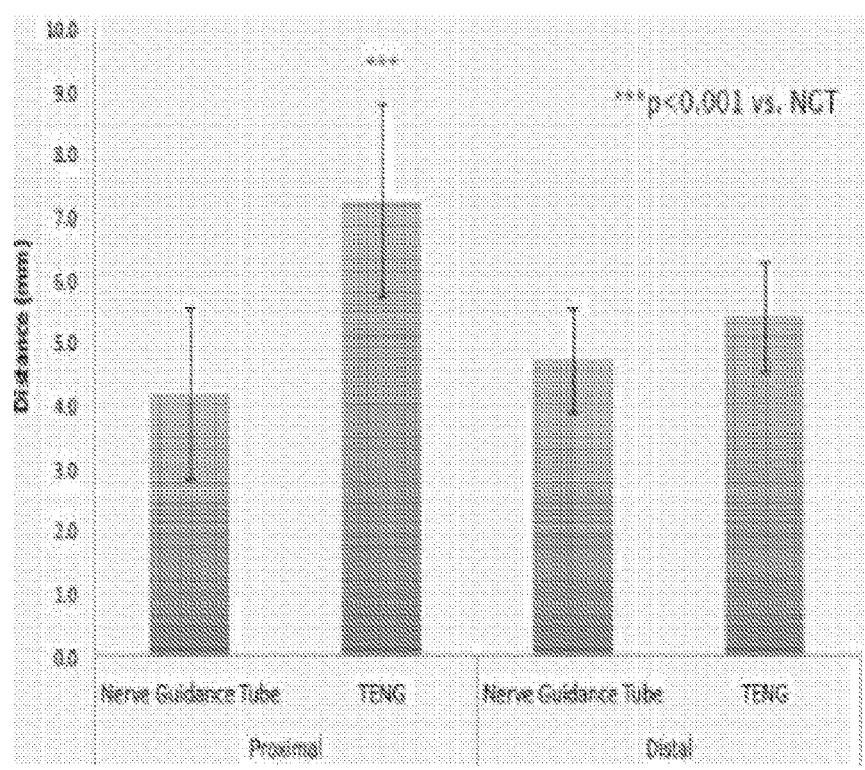

TENGs enhanced Schwann cell infiltration into the nerve gap as compared to NGTs ((FIG. 17 bar graph; $p<0.001$), and reconnection of proximal and distal Schwann cells were observed in TENGs but not NGT groups (FIG. 17, top two panels, in which cables of Schwann cells appear in the TENG group). In NGT groups, Schwann cells infiltrated linearly from the ends, typically observed only in the center of NGT (FIG. 18B, box B, arrow pointing to tapered cone). In TENG groups, TENG axons were visible in the upper quadrant of the section (FIG. 18A, box A), and Schwann cell infiltration was markedly directed upward toward the TENG axons. Thus, the results indicated that TENGs direct host Schwann cell infiltration.

Figure 18A:
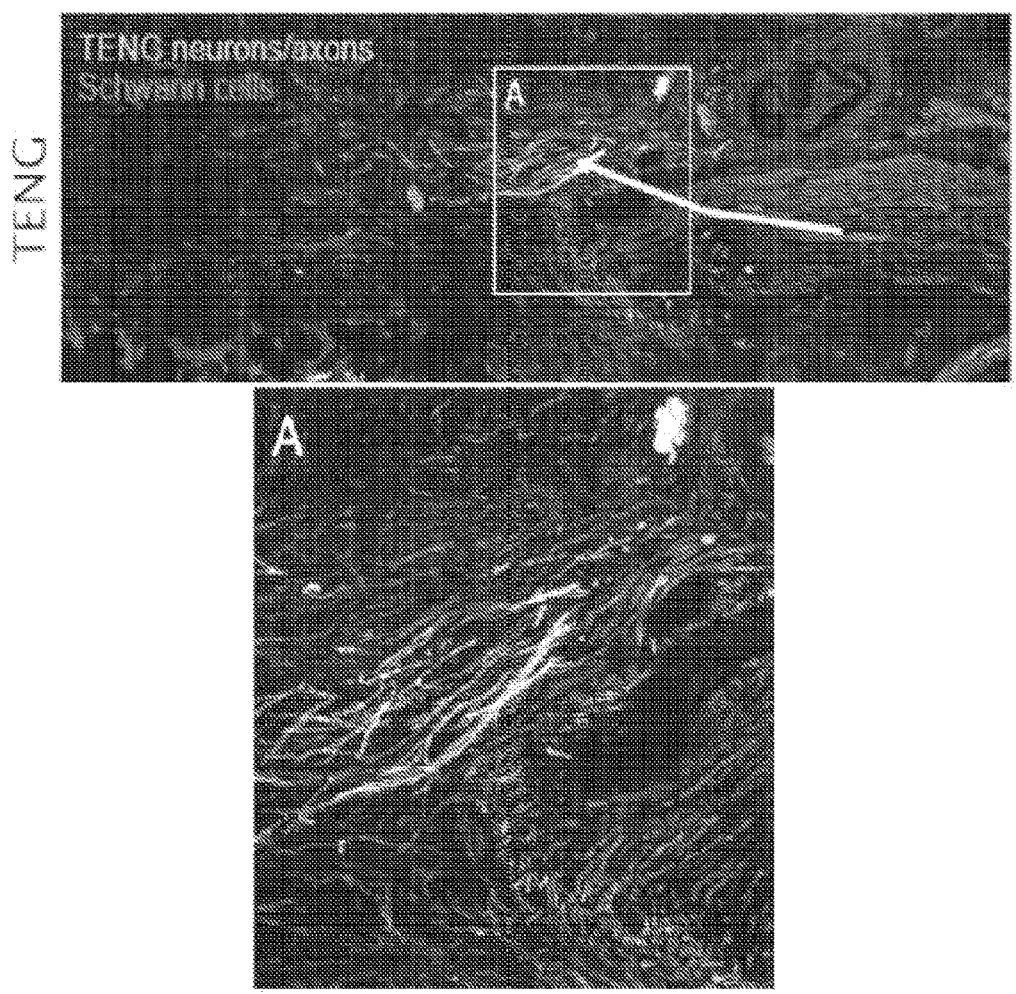
FIGS. 18A-18B, shows Schwann cell infiltration in TENG (FIG. 18A) versus NGT (FIG. 18B). When TENGs are placed off-center, host Schwann cells migrate out of their way to grow along TENG neurons and axons.
Figure 18B:
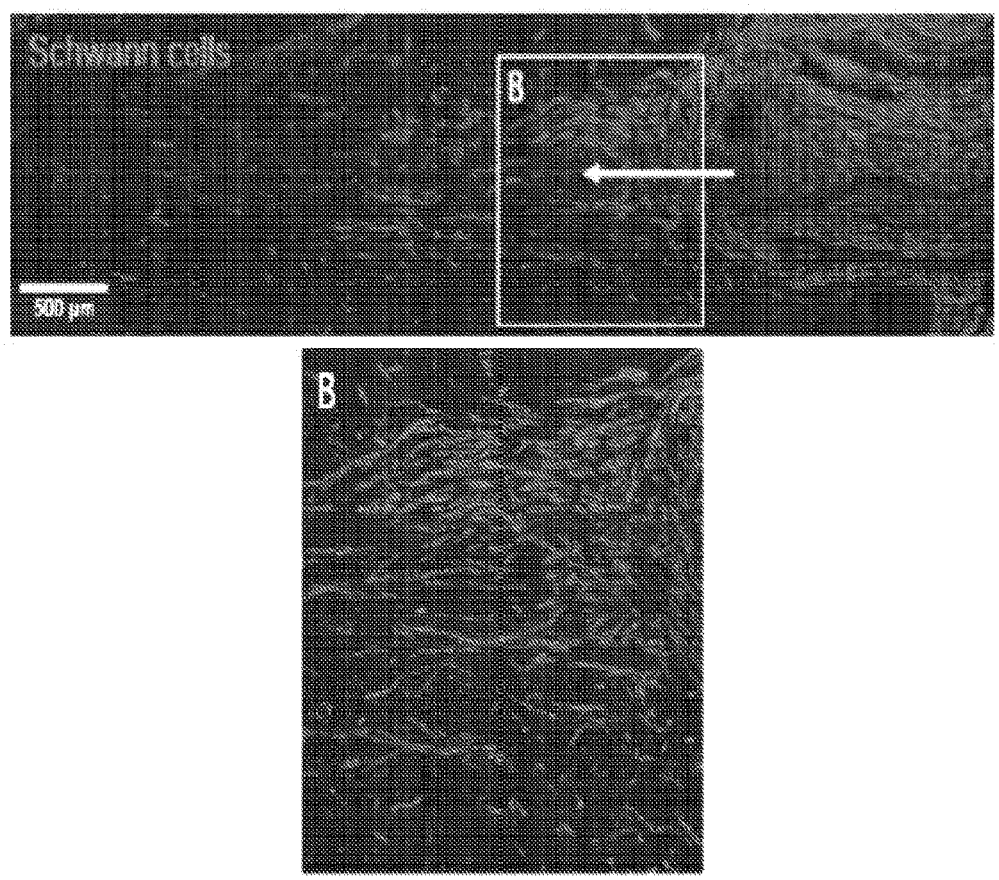
Figure 19:
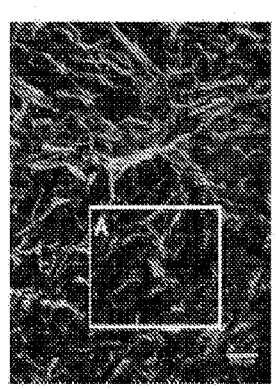
FIG. 19 shows TENG axons, host axons, and Schwann cells in TENG groups. Arrow indicates host axonal regeneration occurring directly along TENG axons; arrowheads indicate pro-regenerative alignment of Schwann cells along TENG axons.
Figure 19:
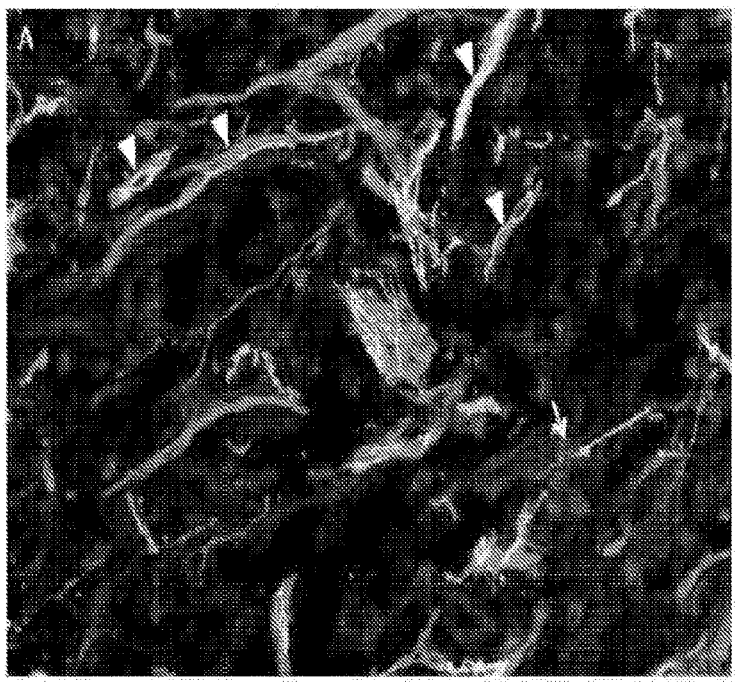

Overall, TENGs appeared to serve as living scaffolds to facilitate acute nerve regeneration by two means: axon-induced axon growth, wherein host axonal regeneration occurred directly along TENG axons in the absence of Schwann cells (FIG. 19, arrow in box A); and enhanced traditional Schwann cell-mediated axonal regeneration, wherein TENG axons increased Schwann cell infiltration and enhanced Schwann cell pro-regenerative alignment (FIG. 18A, arrowheads in Box A).

The results of the study indicated that TENGs possess a novel, superior mechanism of action compared to NGTs and autografts. TENGs induced axon-induced axon growth, increased Schwann cell infiltration and the presence of pioneer axons, and, importantly, maintained, or babysat, the distal pathway.

Example 3. TENG Axons Penetrate into the Distal Nerve Stump at 2 Weeks Post-Transplant TENGs were implanted in a rat sciatic nerve injury as described above in Examples 1 and 2. In this study, TENGs were transduced to express green fluorescent protein (GFP) and the nerve lesion was a 1 cm nerve lesion. Animals were euthanized at 2 weeks post-repair, and the nerves were processed for histological evaluation and sectioned longitudinally. Schwann cells were stained with S100.

Figure 20:
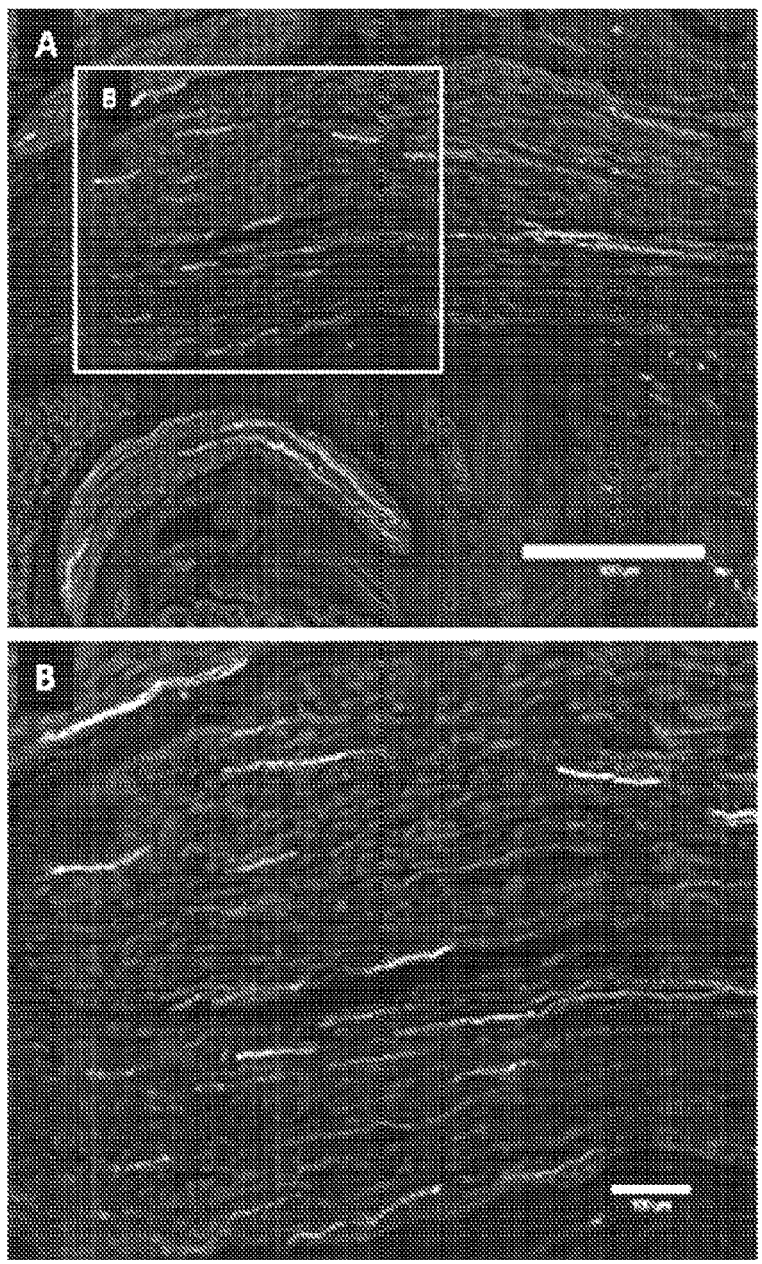
FIG. 20 shows longitudinal sections of GFP+ TENGs projecting numerous axons into the distal nerve stump at 2 weeks post TENG transplant.

Longitudinal tissue sections showed that neurons in the TENG project axons away from the graft and into the distal nerve stump to grow along host Schwann cells (FIG. 20A). FIG. 20B shows a higher magnification of the indicated region in FIG. 20A, and depicts TENG axon interaction and growth along host Schwann cells. There are few host axons in the distal nerve segment at this time point (given this defect length), indicating that TENG axons were the first to penetrate the distal nerve in order to interact with the host Schwann cells. The results of the study showed that TENGs may be used to maintain the pro-regenerative efficacy of the host Schwann cells and thus extend the living pathway necessary for nerve regeneration. In cases where TENGs are used for primary lesion repair for even longer defects (>3 cm), then TENG axons projecting into the distal nerve segment would likely be the only axons interacting with distal Schwann cells for several months until host axons cross the graft, thus maintaining the pro-regenerative efficacy of these Schwann cells absent a second surgical site.

Example 4. TENG Axons Persist within the Distal Nerve Stump at Least Out to 12 Weeks Post-Transplant GFP+ TENGs were implanted in a rat sciatic nerve injury as described above in Example 3. In this study, the nerve lesion was a 2 cm nerve lesion. Animals were euthanized at 12 weeks post-repair, and the nerves were processed for histological evaluation and nerves were processed for histological evaluation and sectioned axially.

Figure 21:
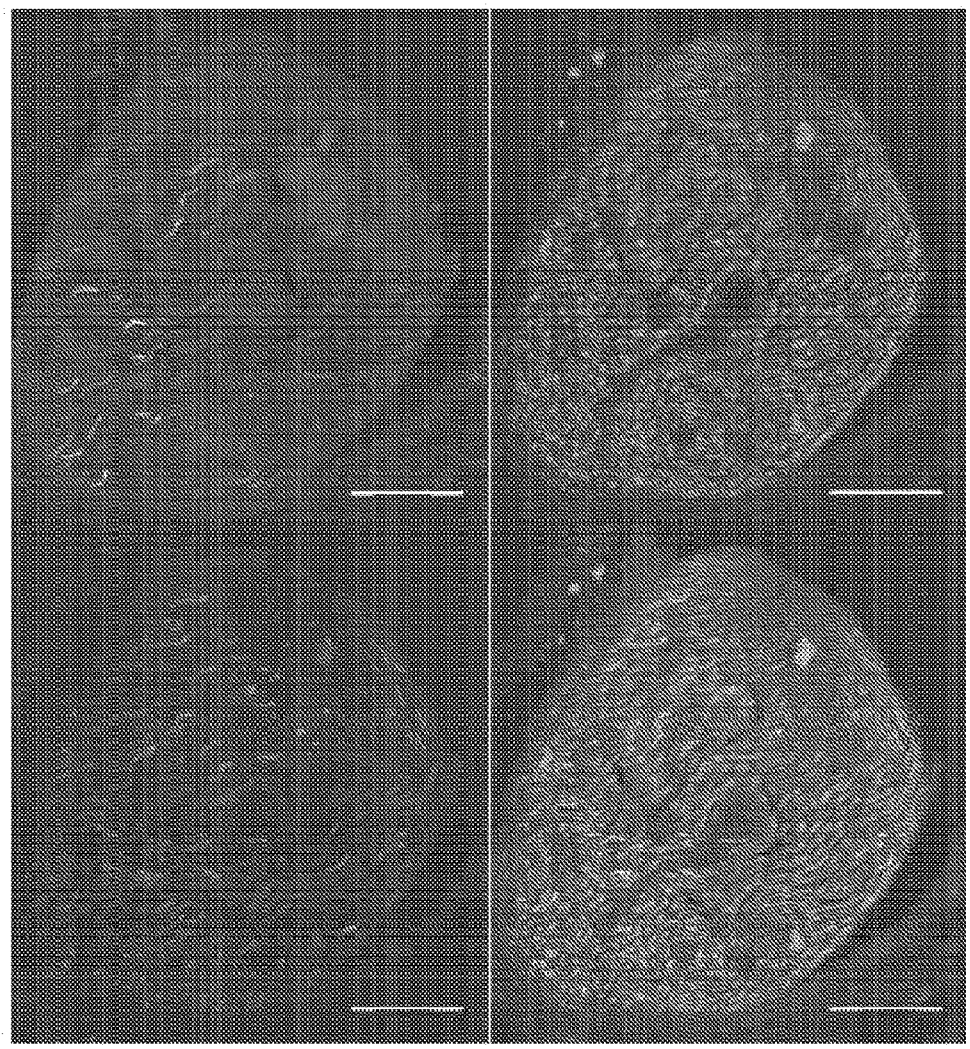
FIG. 21 shows cross-sectional sections of GFP+ TENGs persisting within the distal nerve stump and interacting with host Schwann cells at 12 weeks post TENG transplant.

Nerve cross-sections showed that axons projecting from TENG neurons persisted within the distal nerve stump to interact with host Schwann cells. FIG. 21 shows TENG axons (GFP+, top left panel), host Schwann cells (labeled red via immunohistochemistry for S100; top right panel), axons (labeled purple for neurofilament; bottom left panel), and an overlay of all three channels (bottom right panel). The results of the study showed that TENG axons persist over 12 weeks, indicating that TENG axons can survive long enough to maintain the pro-regenerative efficacy of host Schwann cells (for example, in the absence of host axons).

Example 5. Maintenance of the Distal Nerve Segment Via Direct Injection of Neurons In this study, neurons are injected into a distal nerve segment following nerve injury. Neurons are injected directly into the distal nerve segment or are injected into a conduit or device that directly interfaces with the distal nerve segment. The injection of neurons may be coupled with a primary procedure for nerve repair (e.g., implantation of a stretch-grown TENG at the proximal position of the nerve injury). The outcome of the injection is measured by immunohostochemistry (e.g., staining for Schwann cells to determine morphology and phenotype, as well as staining for axons to determine the extent of regeneration of axons post-nerve injury) or extent of restoration of nerve function. The results of the study will show that neurons injected directly into the distal nerve segment or into a conduit or device that directly interfaces with the distal nerve segment maintain pro-regenerative capacity of distal nerve segments and thereby babysit the distal nerve.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

1. Gordon T, Tyreman N, Raji M A. J Neurosci. 2011 Apr. 6; 31(14):5325-34. doi: 10.1523/JNEUROSCI.6156-10.2011. PMID: 21471367
2. Gordon T, Chan K M, Sulaiman O A, Udina E, Amirjani N, Brushart T M. Neurosurgery. 2009 October; 65(4 Suppl):A132-44. doi: 10.1227/01.NEU.0000335650.09473.D3. Review. PMID: 19927058
3. Sulaiman O A, Gordon T. Neurosurgery. 2009 October; 65(4 Suppl):A105-14. doi: 10.1227/01.NEU.0000358537.30354.63. Review. PMID: 19927054
4. Gordon T. J Commun Disord. 2010 July-August; 43(4): 265-73. doi: 10.1016/j.jcomdis. 2010.04.003. Epub 2010 Apr. 8. PMID: 20451212
5. Gordon T, Chan K M, Sulaiman O A, Udina E, Amirjani N, Brushart T M. Neurosurgery. 2009 October; 65(4 Suppl):A132-44. doi: 10.1227/01.NEU.0000335650.09473.D3. Review. PMID: 19927058
6. Gordon T, Udina E, Verge V M, de Chaves E I. Motor Control. 2009 October; 13(4):412-41. Review. PMID: 20014648
7. Midha R, Munro C A, Chan S, Nitising A, Xu Q G, Gordon T. Neurosurgery. 2005 December; 57(6):1289-99; discussion 1289-99. PMID: 16331178
8. Ladak A, Schembri P, Olson J, Udina E, Tyreman N, Gordon T. Neurosurgery. 2011 June; 68(6):1654-65; discussion 1665-6. doi: 10.1227/NEU.0b013e31821246a8. PMID: 21346654
9. Sulaiman O A, Gordon T. Neurosurgery. 2009 October; 65(4 Suppl):A105-14. doi: 10.1227/01.NEU.0000358537.30354.63. Review. PMID: 19927054

10. Smith, D (2009) Stretch Growth of Integrated Axon Tracts: Extremes & Exploitations; Progress in Neurobiology. 89: 231-239.
11. Farber S. J, Glaus S. W., Moore A. M., Hunter D. A., Mackinnon, S. E., and Johnson P. J. J Hand Surg 2013
12. Barbour J., Yee A., Kahn L C, Mackinnon S E. J Hand Surg 2013; 37A:2150-2159.
13. Scholz T et al., (2009) Peripheral nerve injuries: An international survey of current treatments and future perspectives. J Reconstructive Microsurgery 25(6): 339-344

What is claimed is:

1. A method for maintaining the pro-regenerative capacity of a distal nerve segment subsequent to a nerve injury, the method comprising transplanting a stretch-grown tissue engineered nerve graft (TENG) into a distal site in the distal nerve segment,
wherein the TENG facilitates axon growth and Schwann cell infiltration, thereby maintaining the pro-regenerative capacity of the distal nerve segment;
and wherein the nerve injury occurs as a result of trauma, a surgical procedure, the positioning of a patient during surgery, a compression or crush injury, a disease related to a loss of motor or sensory nerve function, a congenital anomaly, an amputation, complete or partial removal of an organ, tumor or tissue, a metabolic/endocrine complication, inflammatory disease, autoimmune disease, vitamin deficiency, infectious disease, toxin, exposure to organic metal or heavy metal, or administration of a medication or drug.

2. The method of claim 1, wherein the nerve injury is present in a subject.

3. The method of claim 2, wherein the subject is a human.

4. The method of claim 2, wherein the subject is a non-human mammal.

5. The method of claim 1, wherein the nerve injury comprises an injury to a peripheral nerve of a subject.

6. The method of claim 1, wherein the nerve injury comprises an injury to the spinal cord of a subject.

7. The method of claim 1, wherein the nerve injury comprises the loss of a segment of nerve.

8. The method of claim 1, wherein the nerve injury comprises a nerve lesion of less than about 1 cm in length.

9. The method of claim 1, wherein the nerve injury comprises a nerve lesion of at least about 1 cm in length.

10. The method of claim 1, wherein the nerve injury comprises a nerve lesion of at least about 3 cm in length.

11. The method of claim 1, wherein the nerve injury comprises a nerve lesion of at least 5 cm in length.

12. The method of claim 1, wherein the nerve injury comprises multiple nerve lesions.

13. The method of claim 1, wherein the pro-regenerative capacity of the distal nerve segment is maintained for at least about 12 weeks.

14. The method of claim 1, wherein the pro-regenerative capacity of the distal nerve segment is maintained until at least such time as proximal nerve axons regenerate across the nerve injury.

15. The method of claim 1, wherein pro-regenerative capacity of the distal nerve segment is maintained until at least such time as proximal nerve axons reinnervate distal targets.

16. The method of claim 1, wherein the method further comprises a primary procedure for nerve repair.

17. The method of claim 16, wherein the method results in a greater degree of functional recovery following repair of PNI, as compared to the degree of functional recovery that occurs following the primary procedure alone.

18. The method of claim 1, wherein the method is conducted in the absence of any other nerve repair.

19. The method of claim 1, further comprising providing a neurotrophic factor, culture supernatant, or cells to the distal nerve segment.

20. The method of claim 19, wherein the cells are selected from the group consisting of neurons, and stem cells.

21. The method of claim 1, wherein the method does not comprise transecting a nearby healthy nerve or the repaired nerve.

22. The method of claim 1, wherein the method enhances the survival of Schwann cells in the distal nerve segment.

23. The method of claim 1, wherein the distal site is at least about 3 cm away from the site of injury.

24. The method of claim 1, wherein the distal site is less than least about 3 cm away from the site of injury.

25. The method of claim 1, wherein the method comprises contacting multiple distal nerve segments with one or more stretch-grown TENG.

* * * * *

UNITED STATES PATENT AND TRADEMARK OFFICE
CERTIFICATE OF CORRECTION

PATENT NO. : 9,895,399 B2  
APPLICATION NO. : 14/764450  
DATED : February 20, 2018  
INVENTOR(S) : Douglas H. Smith, Kacy D. Cullen and John A. Wolf Page 1 of 1

It is certified that error appears in the above-identified patent and that said Letters Patent is hereby corrected as shown below:

In the Specification

In Column 1, after the heading "STATEMENT REGARDING FEDERALLY SPONSORED RESEARCH OR DEVELOPMENT," please replace the paragraph at Lines 18-24 with the following paragraph:
--This invention was made with government support under W81XWH-16-1-0796, and W81XWH-10-1-0941 awarded by the United States Army Medical Research and Development Command, and NS056202, NS038104, and NS048949 awarded by the National Institutes of Health. The government has certain rights in the invention.--

Signed and Sealed this  
Twenty-sixth Day of December, 2023

Katherine Kelly Vidal  
*Director of the United States Patent and Trademark Office*